(12) United States Patent
Matsumoto et al.

(10) Patent No.: US 11,499,133 B2
(45) Date of Patent: *Nov. 15, 2022

(54) CELL TREATMENT APPARATUS AND METHOD FOR TREATING OBJECT TO BE TREATED

(71) Applicant: KATAOKA CORPORATION, Kyoto (JP)

(72) Inventors: Junichi Matsumoto, Kyoto (JP); Shoichi Honda, Kyoto (JP)

(73) Assignee: KATAOKA CORPORATION, Kyoto (JP)

( * ) Notice: Subject to any disclaimer, the term of this patent is extended or adjusted under 35 U.S.C. 154(b) by 195 days.

This patent is subject to a terminal disclaimer.

(21) Appl. No.: 16/485,367

(22) PCT Filed: Sep. 20, 2017

(86) PCT No.: PCT/JP2017/033964
§ 371 (c)(1),
(2) Date: Aug. 12, 2019

(87) PCT Pub. No.: WO2018/146855
PCT Pub. Date: Aug. 16, 2018

(65) Prior Publication Data
US 2020/0032198 A1    Jan. 30, 2020

(30) Foreign Application Priority Data
Feb. 13, 2017 (JP) .............................. JP2017-024512

(51) Int. Cl.
*C12M 1/00* (2006.01)
*C12M 1/12* (2006.01)
(Continued)

(52) U.S. Cl.
CPC .......... *C12M 47/04* (2013.01); *C12M 1/3446* (2013.01); *C12M 25/06* (2013.01);
(Continued)

(58) Field of Classification Search
None
See application file for complete search history.

(56) References Cited

U.S. PATENT DOCUMENTS 4,301,252 A   11/1981   Baker et al.
5,792,427 A   8/1998    Hugh et al.
(Continued)

FOREIGN PATENT DOCUMENTS

CN   1154475    7/1997
CN   1251528    4/2000
(Continued)

OTHER PUBLICATIONS

Extended European Search Report issued in European Patent Application No. 17896294.0, dated Oct. 22, 2020, 8 pages.
(Continued)

*Primary Examiner* — William H. Beisner
(74) *Attorney, Agent, or Firm* — Hamre, Schumann, Mueller & Larson, P.C.

(57) ABSTRACT

The present invention provides a cell treatment apparatus capable of treating cells in a cell culture vessel. The cell treatment apparatus 100 according to the present invention includes a first region 1, a second region 3, and a third region 5. The first region 1 and the second region 3 are placed in succession. The first region 1 is a cell treatment chamber for treating cells. The cell treatment chamber can be closed from the outside of the cell treatment chamber and includes a culture vessel placement portion for placing a cell culture vessel. The second region 3 includes: a laser irradiation device capable of irradiating the cell culture vessel placed in
(Continued)

the culture vessel placement portion with a laser; and a spot diameter adjustment device that adjusts a spot diameter formed in a portion to be irradiated with the laser in an object to be irradiated. The third region 5 includes a control device that controls at least one device in the cell treatment apparatus 100 and a power supply device 52 that supplies electric power to at least one device in the cell treatment apparatus 100. The culture vessel placement portion is placed to be adjacent to the second region 3 in the cell treatment chamber. An adjacent portion to the second region 3 in the culture vessel placement portion is translucent.

9 Claims, 8 Drawing Sheets

(51) Int. Cl.

| | | |
|---|---|---|
| *C12M 1/42* | (2006.01) | |
| *C12M 1/33* | (2006.01) | |
| *C12N 13/00* | (2006.01) | |
| *C12N 5/074* | (2010.01) | |
| *C12N 5/00* | (2006.01) | |
| *C12N 5/0735* | (2010.01) | |
| *C12M 1/34* | (2006.01) | |
| *G01N 21/64* | (2006.01) | |

(52) U.S. Cl.
CPC ............ *C12M 35/02* (2013.01); *C12M 41/10* (2013.01); *C12M 45/02* (2013.01); *C12N 5/00* (2013.01); *C12N 5/0606* (2013.01); *C12N 5/0696* (2013.01); *C12N 13/00* (2013.01); *G01N 21/64* (2013.01)

(56) References Cited

U.S. PATENT DOCUMENTS

| | | | |
|---|---|---|---|
| 5,874,266 A | | 2/1999 | Palsson |
| 6,033,396 A | * | 3/2000 | Huang .................... A61F 9/008 606/10 |
| 6,143,535 A | | 11/2000 | Palsson |
| 6,281,670 B1 | | 8/2001 | Sugihara et al. |
| 6,699,238 B1 | * | 3/2004 | Sagehashi ............... A61F 9/008 606/10 |
| 2001/0005586 A1 | | 6/2001 | Palsson et al. |
| 2002/0076744 A1 | | 6/2002 | Koller et al. |
| 2002/0177885 A1 | | 11/2002 | Eisfeld et al. |
| 2003/0031602 A1 | | 2/2003 | Weselak et al. |
| 2003/0148393 A1 | | 8/2003 | Woodbury |
| 2004/0043392 A1 | | 3/2004 | Washiyama et al. |
| 2004/0063195 A1 | | 4/2004 | Tamaoki et al. |
| 2005/0095578 A1 | | 5/2005 | Koller et al. |
| 2005/0202558 A1 | | 9/2005 | Koller et al. |
| 2005/0276456 A1 | | 12/2005 | Yamato et al. |
| 2007/0160280 A1 | | 7/2007 | Schutze et al. |
| 2008/0057558 A1 | * | 3/2008 | Niwa .................. G02B 21/0088 435/173.9 |
| 2010/0328434 A1 | * | 12/2010 | Kiyota .................... C12M 41/46 348/46 |
| 2013/0023025 A1 | | 1/2013 | Sumaru et al. |
| 2013/0045187 A1 | | 2/2013 | Semechkin et al. |
| 2013/0327195 A1 | | 12/2013 | Routamaa et al. |
| 2014/0099695 A1 | | 4/2014 | Furuta et al. |
| 2015/0044770 A1 | | 2/2015 | Kim |
| 2018/0142193 A1 | | 5/2018 | Suzuki et al. |
| 2018/0354076 A1 | | 12/2018 | Suzuki et al. |
| 2018/0356321 A1 | | 12/2018 | Sase |
| 2020/0325432 A1 | | 10/2020 | Matsumoto |

FOREIGN PATENT DOCUMENTS

| | | |
|---|---|---|
| CN | 103354896 | 10/2013 |
| CN | 103502425 | 1/2014 |
| CN | 203663257 U | 6/2014 |
| EP | 1 784 633 | 5/2007 |
| EP | 3 467 091 | 4/2019 |
| JP | 4-356183 | 12/1992 |
| JP | 2002-511843 | 4/2002 |
| JP | 2003-284549 | 10/2003 |
| JP | 2004-113153 | 4/2004 |
| JP | 2004-350641 | 12/2004 |
| JP | 2005-333889 | 12/2005 |
| JP | 2007-514407 | 6/2007 |
| JP | 2009-082144 | 4/2009 |
| JP | 2009-195110 | 9/2009 |
| JP | 2010-154793 | 7/2010 |
| JP | 4512206 B | 7/2010 |
| JP | 4728319 6 | 7/2011 |
| JP | 2011-206066 | 10/2011 |
| JP | 2012-130341 | 7/2012 |
| JP | 5087192 6 | 11/2012 |
| JP | 2014-064518 | 4/2014 |
| JP | 2014-509192 | 4/2014 |
| JP | 5580755 B | 8/2014 |
| JP | 6033980 B | 11/2016 |
| JP | 2017-012027 | 1/2017 |
| NO | 2006/024819 | 3/2006 |
| NO | 2017/002422 | 1/2017 |
| WO | 2004/037968 | 5/2004 |
| WO | 2006/088154 | 8/2006 |
| WO | 2011/125615 | 10/2011 |
| WO | 2016/194454 | 12/2016 |
| WO | 2017/208589 | 12/2017 |
| WO | 2018/047702 | 3/2018 |

OTHER PUBLICATIONS

Office Action issued in U.S. Appl. No. 15/576,228, dated Oct. 7, 2019, 11 pages.
Hohenstein Elliott, K. A., et al., "Laser-Based Propagation of Human iPS and ES Cells Generates Reproducible Cultures with Enhanced Differentiation Potential", Stem Cells International, 2012, vol. 2012, Article ID: 926463, pp. 1-13.
Office Action of the corresponding Japanese Patent Application (No. 2017-024511) dated Jan. 22, 2019, 12 pages with translation.
Office Action of the corresponding Japanese Patent Application (No. 2017-024512) dated Jan. 22, 2019, 11 pages with translation.
International Search Report issued in International Application No. PCT/JP2017/033963, dated Dec. 19, 2017, 5 pages with translation.
International Search Report issued in International Application No. PCT/JP2017/033964, dated Dec. 26, 2017, 5 pages with translation.
Extended European Search Report in the related European Patent Application No. 19826059.8, dated Mar. 4, 2022, 7 pages.
Office Action issued in co-pending U.S. Appl. No. 16/485,356 dated Dec. 22, 2021, 19 pages.

\* cited by examiner

CELL TREATMENT APPARATUS AND METHOD FOR TREATING OBJECT TO BE TREATED

TECHNICAL FIELD

The present invention relates to a cell treatment apparatus and a method for treating an object to be treated.

BACKGROUND ART

In recent years, attempts have been made to differentiate target cells, tissues, and the like from pluripotent cells such as induced pluripotent stem cells (iPS cells) and embryonic stem cells (ES cells) and to utilize them for regenerative medicine and drug discovery.

In maintaining the pluripotent cells, some of the proliferating pluripotent cells may differentiate into other cells. In addition, in differentiation from pluripotent cells to target cells or the like, some of differentiated cells may differentiate into cells that are not the target cells.

In such a case, the removal of cells other than the target cells is currently performed manually. However, this removing operation requires time and labor, for example, to be carried out under a microscope, and there is a problem that the quality of cells and the like obtained differs greatly depending on the skill level of the operator (Patent Literature 1).

CITATION LIST

Patent Literature

Patent Literature 1: JP 2014-509192 A

SUMMARY OF INVENTION

Technical Problem

Hence, a first object of the present invention is to provide a cell treatment apparatus capable of treating cells in a cell culture vessel.

A second object of the present invention is to provide a method for treating an object to be treated including a light-absorbing layer and a culture existing above the light-absorbing layer.

Solution to Problem

In order to achieve the first object, the cell treatment apparatus according to the present invention is configured such that it includes: a first region; a second region; and a third region, the first region and the second region are placed in succession, the first region is a cell treatment chamber for treating cells, the cell treatment chamber can be closed from the outside of the cell treatment chamber and includes a culture vessel placement portion for placing a cell culture vessel, the second region includes: a laser irradiation device capable of irradiating the cell culture vessel placed in the culture vessel placement portion with a laser; and a spot diameter adjustment device that adjusts a spot diameter formed in a portion to be irradiated with the laser in an object to be irradiated, the third region includes: a control device that controls at least one device in the cell treatment apparatus; and a power supply device that supplies electric power to at least one device in the cell treatment apparatus, the culture vessel placement portion is placed to be adjacent to the second region in the cell treatment chamber, and an adjacent portion to the second region in the culture vessel placement portion is translucent.

In order to achieve a second object, a method for treating an object to be treated (hereinafter also referred to as "treatment method") according to the present invention includes: a cutting step of, in an object to be treated including a light-absorbing layer and a culture existing above the light-absorbing layer, irradiating the light-absorbing layer corresponding to a region to be cut in the culture with light to cut the culture existing above the light-absorbing layer into a predetermined shape; and a treating step of irradiating the light-absorbing layer corresponding to a portion other than the region to be cut with light to subject the culture existing above the light-absorbing layer to a killing treatment, and a first spot diameter formed in a portion to be irradiated in the light-absorbing layer by the light in the cutting step is different from the second spot diameter formed in a portion to be irradiated in the light-absorbing layer by the light in the treating step.

Advantageous Effects of Invention

The cell treatment apparatus according to the present invention is capable of treating cells in the cell culture vessel.

By the treatment method according to the present invention, an object including a light-absorbing layer and a culture existing above the light-absorbing layer can be treated.

DESCRIPTION OF EMBODIMENTS

Figure 1:
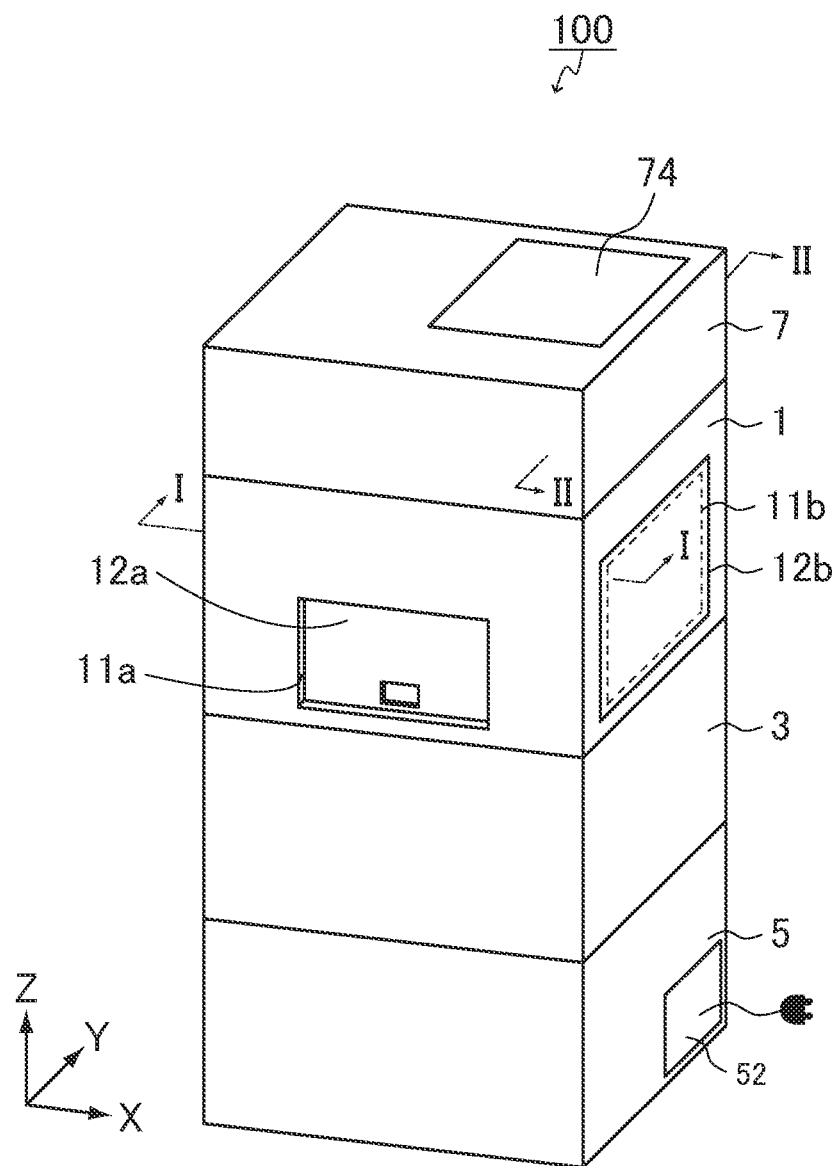
FIG. 1 is a perspective view illustrating an example of the cell treatment apparatus according to the first embodiment.

In the cell treatment apparatus according to the present invention, the laser irradiation device includes, for example, multiple lenses, and the spot diameter adjustment device adjusts the spot diameter by switching the lens.

In the cell treatment apparatus according to the present invention, the spot diameter adjustment device adjusts the spot diameter by adjusting the distance between the laser irradiation device and the object to be irradiated, for example.

In the cell treatment apparatus according to the present invention, the control device includes a spot diameter adjustment control unit that controls the adjustment of the spot diameter performed by the spot diameter adjustment device, for example.

In the cell treatment apparatus according to the present invention, the first region is placed above the second region, for example.

In the treatment method according to the present invention, the first spot diameter is larger than the second spot diameter, for example.

In the treatment method according to the present invention, the light is laser, for example.

The following describes the cell treatment apparatus according to the present invention in further detail with reference to the drawings. The present invention, however, is by no means limited thereby. In FIGS. 1 to 9 described below, the same portions are denoted by the same reference numerals, and the description thereof may be omitted. In addition, in the drawings, for convenience of description, the structure of each part may be shown in a simplified manner as appropriate, and the dimensional ratio and the like of each part may be schematically shown differently from actual ones.

First Embodiment

Figure 2:
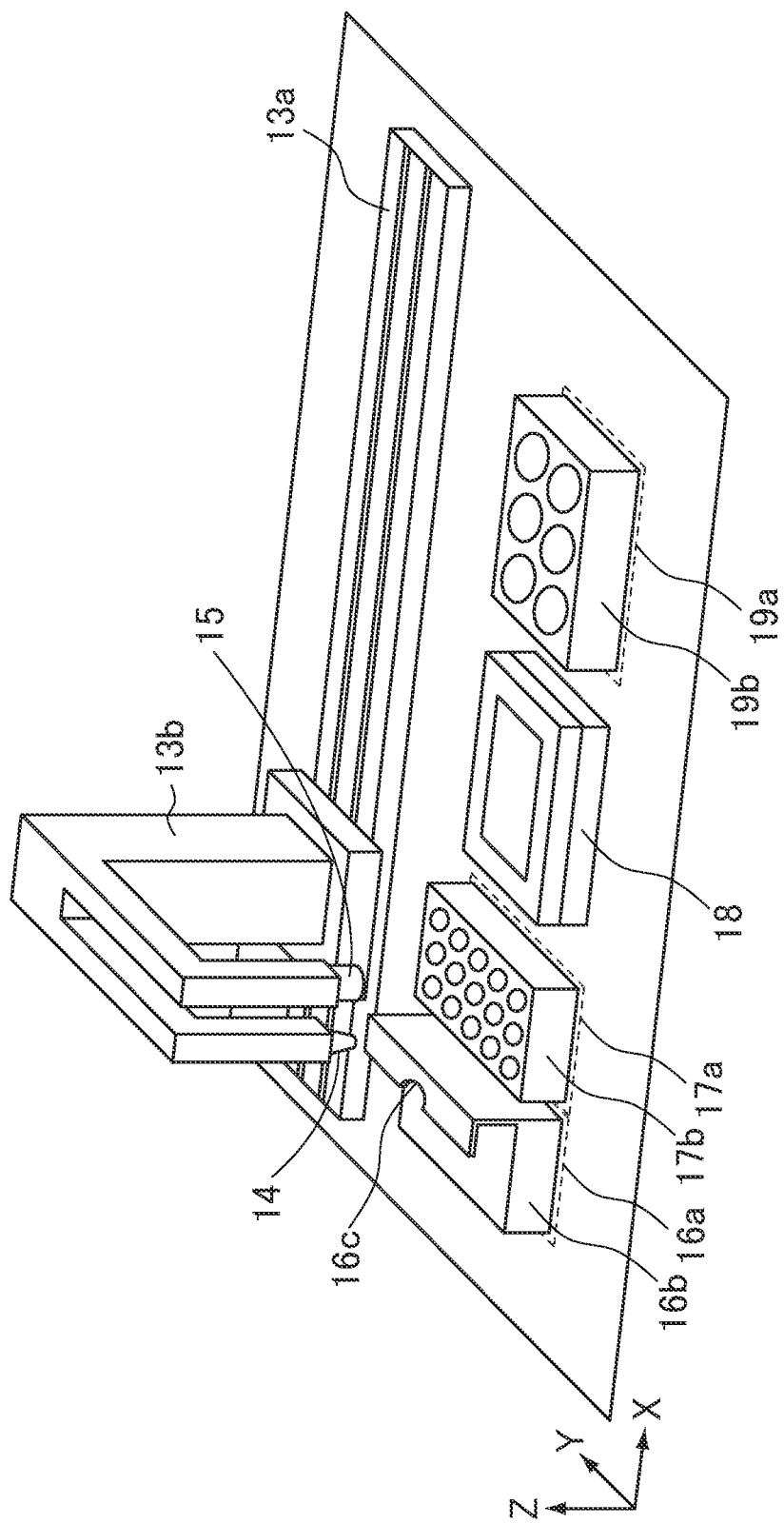
FIG. 2 is a perspective view illustrating an example of the first region in the cell treatment apparatus according to the first embodiment.
Figure 3:
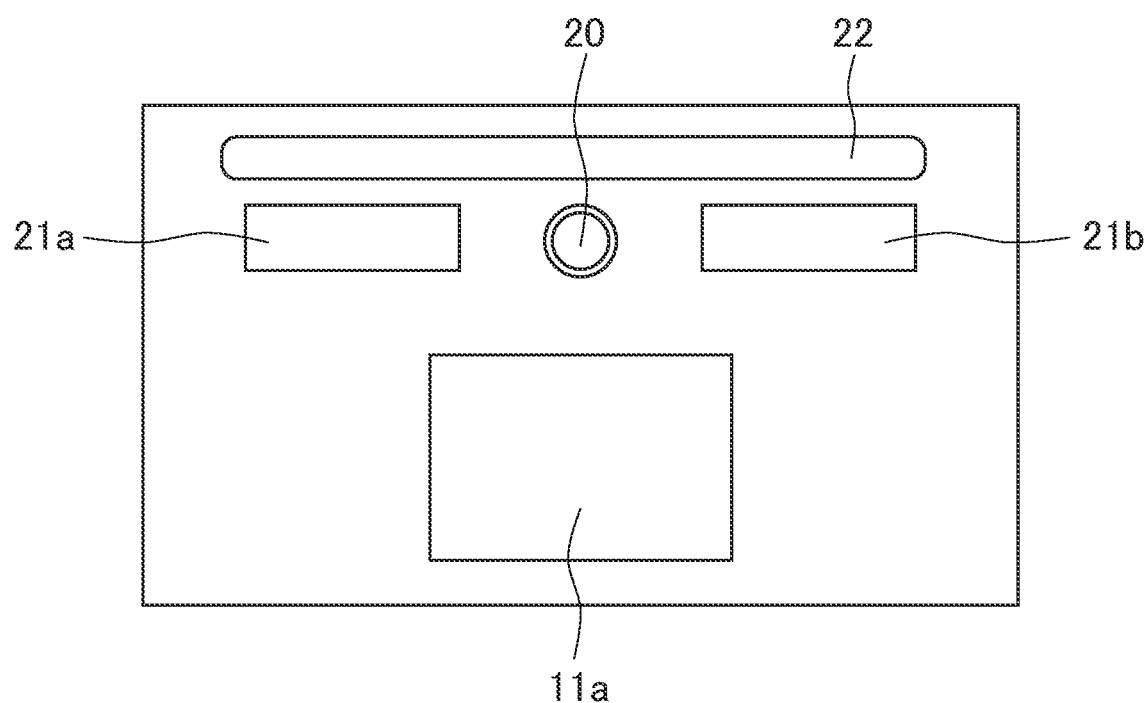
FIG. 3 is a cross-sectional view of the first region as viewed from the I-I direction of FIG. 1.
Figure 4A:
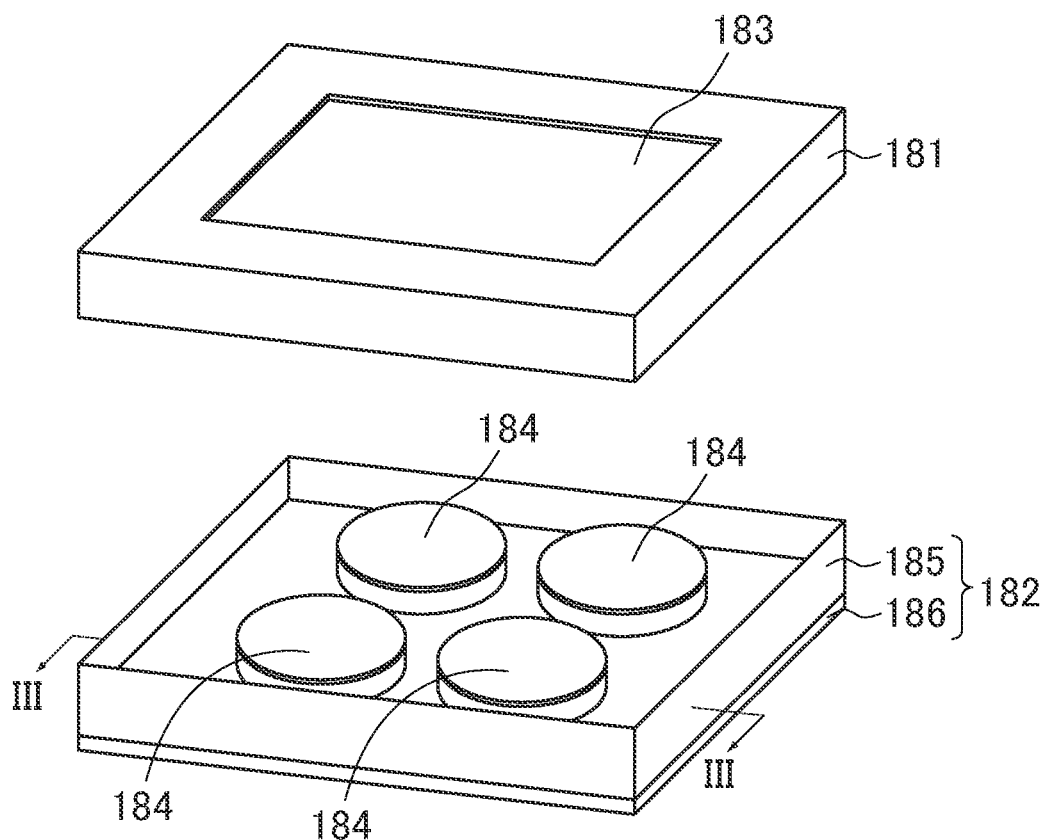
FIG. 4A is an exploded perspective view illustrating an example of the culture vessel placement portion in the cell treatment apparatus according to the first embodiment.
Figure 4B:
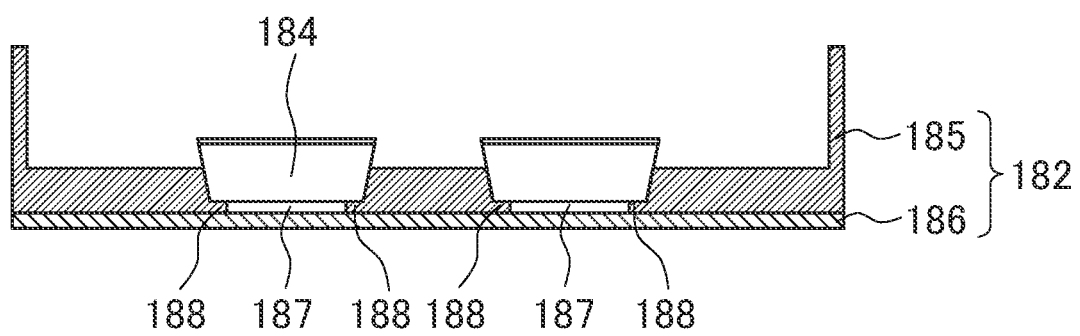
FIG. 4B is a cross-sectional view of the culture vessel placement portion as viewed from the direction of FIG. 4A.
Figure 5:
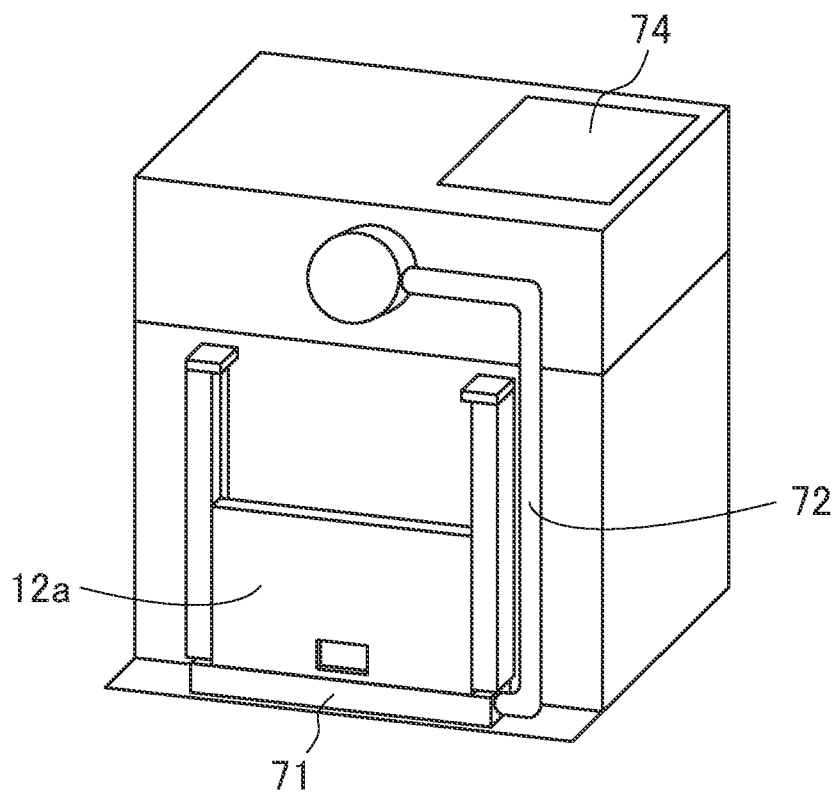
FIG. 5 is a perspective view illustrating an example of the first region and an example of the circulator in the case where an outer wall of the first region has been removed in the cell treatment apparatus according to the first embodiment.
Figure 6:
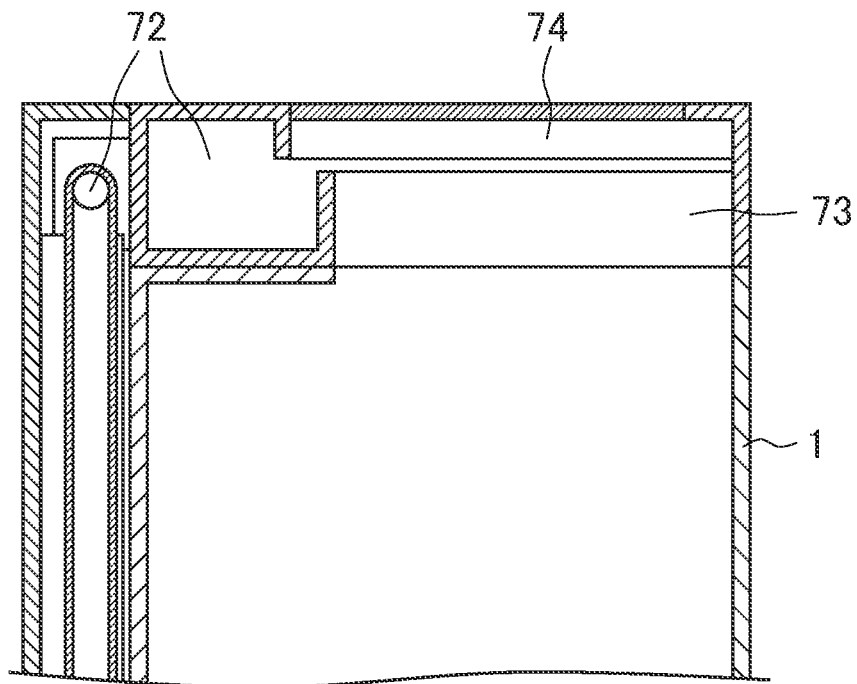
FIG. 6 is a cross-sectional view illustrating an upper part of the first region and the circulator as viewed from the II-II direction of FIG. 1.
Figure 7A:
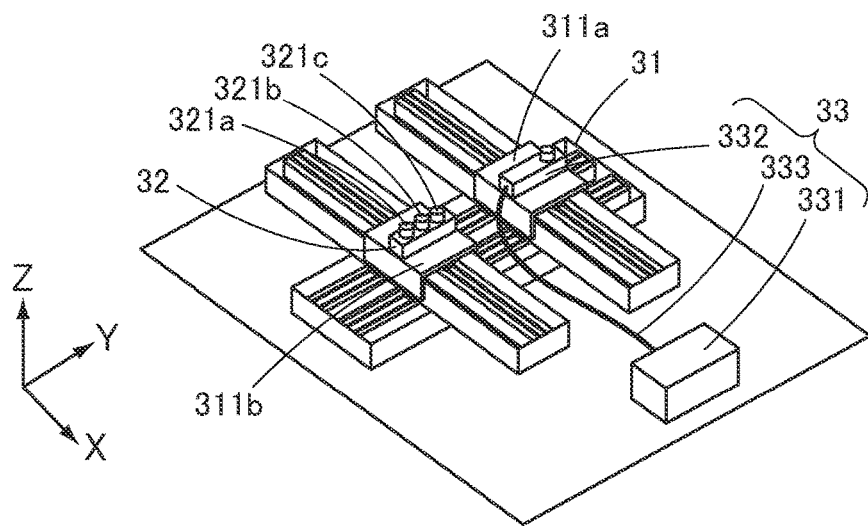
FIG. 7A is a perspective view illustrating an example of the configuration of a second region in the cell treatment apparatus according to the first embodiment.
Figure 7B:
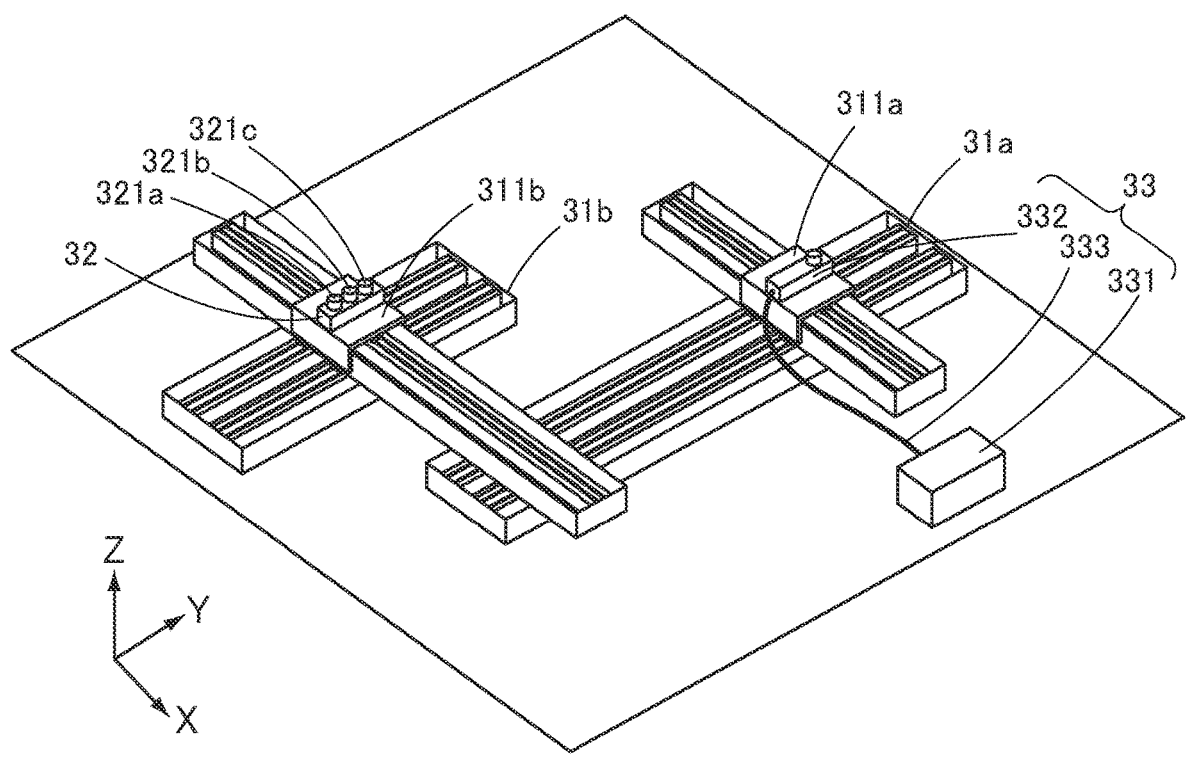
FIG. 7B is a perspective view illustrating another example of the configuration of the second region.
Figure 8:
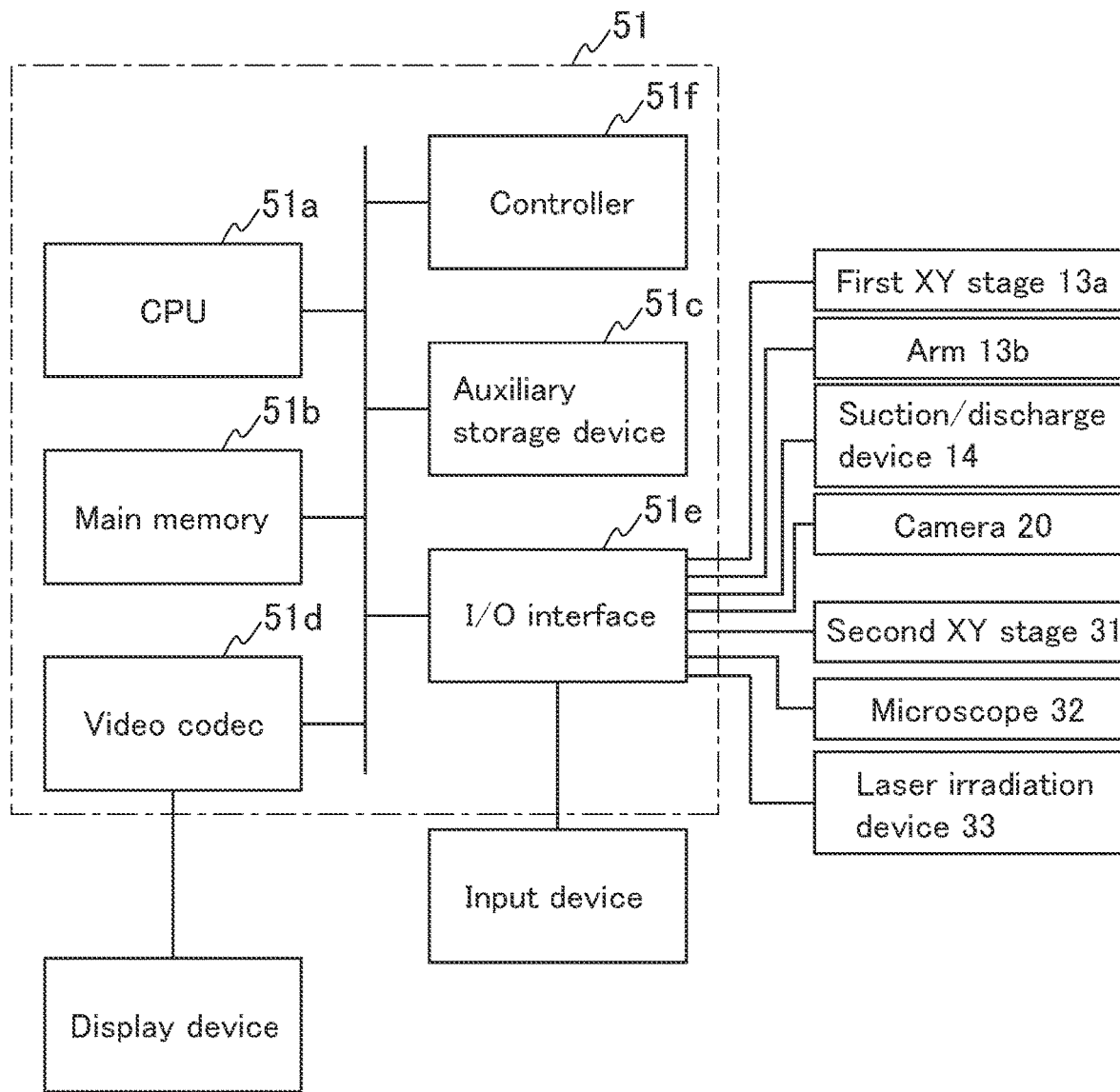
FIG. 8 is a block diagram illustrating an example of the configuration of a control device in the cell treatment apparatus according to the first embodiment.
Figure 9:
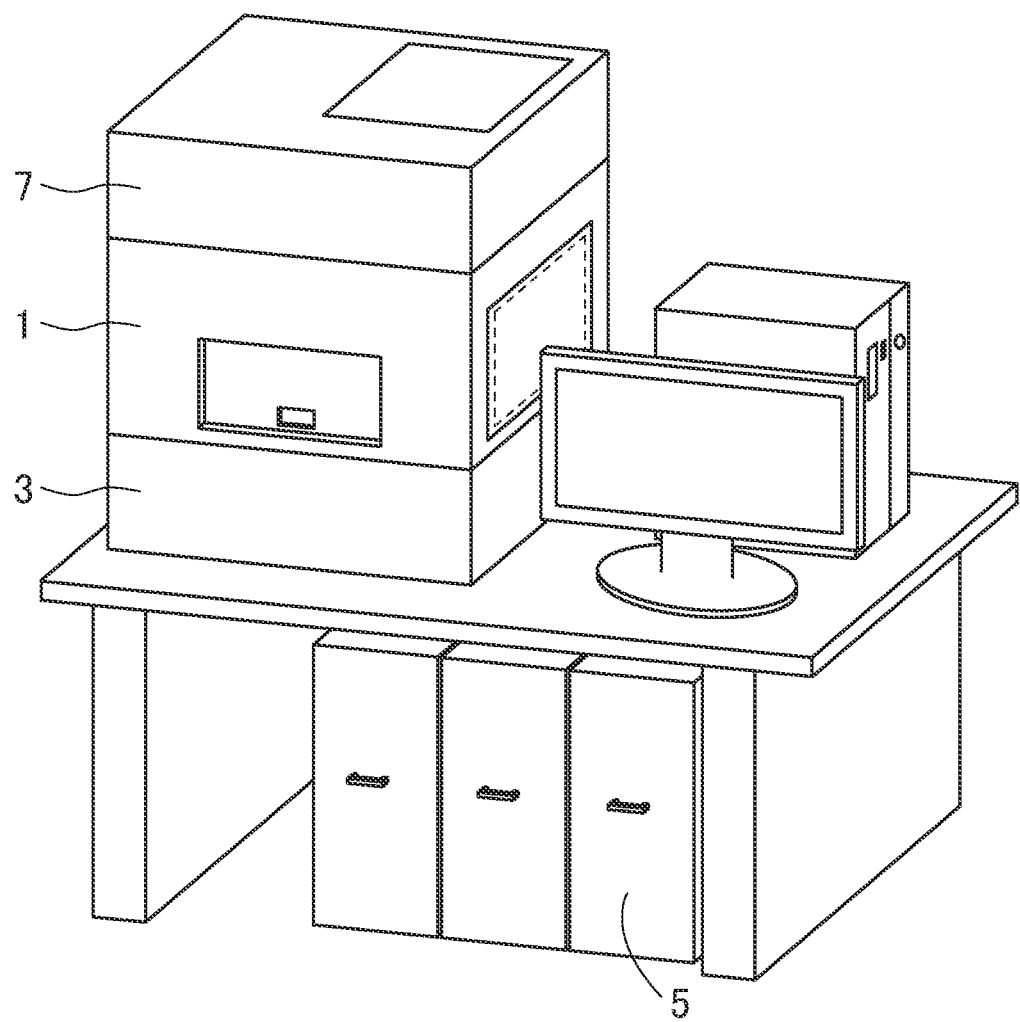
FIG. 9 is a perspective view illustrating another example of the cell treatment apparatus according to the first embodiment.

The present embodiment is an example of the cell treatment apparatus. FIGS. 1 to 9 illustrate an example of the configuration of the cell treatment apparatus according to the present embodiment. FIG. 1 is a perspective view illustrating an example of the cell treatment apparatus according to the present embodiment. FIG. 2 is a perspective view illustrating an example of the configuration of a first region in the cell treatment apparatus according to the present embodiment. FIG. 3 is a cross-sectional view illustrating the example of the configuration of the first region viewed from the I-I direction of FIG. 1. FIG. 4A is an exploded perspective view illustrating an example of the culture vessel placement portion in the cell treatment apparatus according to the present embodiment. FIG. 4B is a cross-sectional view of the culture vessel placement portion as viewed from the direction of FIG. 4A. FIG. 5 is a perspective view illustrating the first region and a circulator in the case where an outer wall of the first region has been removed. FIG. 6 is a cross-sectional view illustrating an upper portion of the first region and the circulator as viewed from the II-II direction of FIG. 1. FIG. 7A is a perspective view illustrating an example of the configuration of a second region of the cell treatment apparatus according to the present embodiment. FIG. 7B is a perspective view illustrating another example of the configuration of the second region. FIG. 8 is a block diagram illustrating an example of the control device in the cell treatment apparatus according to the present embodiment. FIG. 9 is a perspective view illustrating another example of the configuration of the cell treatment apparatus according to the present embodiment.

In the present embodiment, the cell to be treated is not particularly limited, and may be a cell, a cell mass composed of cells, a tissue, an organ, or the like. The cell may be, for example, a cultured cell or a cell isolated from a living body. The cell mass, tissue, or organ may be, for example, a cell mass, tissue, or organ produced from the cell, or may be a cell mass, tissue, or organ isolated from a living body. In the cell treatment apparatus according to the present invention, for example, microorganisms such as bacteria and fungi may be treated instead of the cells. In this case, the cell treatment apparatus according to the present invention can also be referred to as, for example, microorganism treatment apparatus.

As shown in FIG. 1, a cell treatment apparatus 100 according to the present embodiment includes a first region 1, a second region 3, a third region 5, and a circulator 7, and the first region 1, the second region 3, and the third region 5 are placed in succession in this order from the top. The circulator 7 included in the cell treatment apparatus 100 according to the present embodiment is an optional component and may or may not be included. The positional relationship among the first region 1, the second region 3, and the third region 5 may be such that the first region 1 and the second region 3 are placed in succession, and the third region 5 may be placed at any position. The third region 5 may be placed separately from the first region 1 and the second region 3, for example, as shown in FIG. 9. As shown in FIG. 9, in the case where the third region 5 is placed separately from the first region 1 and the second region 3, the cell treatment apparatus 100 can also be referred to as a cell treatment system, for example. The cell treatment system may be, for example, a tabletop system. The first region 1 is preferably placed above the second region 3. When laser irradiation is performed from an upper portion of the cell culture vessel 184 by the laser irradiation device 33, it is required to place an emission port for the laser emission unit 332 in a culture medium inside the cell culture vessel 184 to stabilize the focal point of the laser irradiation device 33. However, when laser irradiation is performed in this state, a problem of baking arises where components of the culture medium are fixed to the emission port for the laser emission unit 332, and the emission port of the laser emission unit 332 is contaminated. Thus, contamination of the emission port for the laser irradiation device 33 can be prevented by placing the laser irradiation device 33 as in the cell treatment apparatus 100 according to the present embodiment when cells in the cell culture vessel 184 are cultured by the laser irradiation device 33 to be described later, for example. Therefore, the cell treatment apparatus 100 according to the present invention is capable of stabilizing the output of the laser emitted from the laser irradiation device 33 and is capable of efficiently treating cells, for example. The material for forming each region is not particularly limited, and examples thereof include a stainless steel plate, a rust-proof iron plate, and a resin plate that can be molded by vacuum molding, injection molding, pressure forming, or the like. The material for forming each region is preferably a non-translucent material because the second imaging device to be described later can more clearly image the cells in the cell culture vessel 184. The "non-translucent" means, for example, to suppress transmission of light having a wavelength that affects imaging by the second imaging device. In the case where the second imaging device is a fluorescence microscope, the wavelength of the light may be, for example, a wavelength corresponding to the fluorescence to be detected. As a specific example, the non-translucent material can be, for example, the above-mentioned material for forming each region. The size and shape of each region are not particularly limited, and can be appropriately set according to the size and shape of each member placed in each region. In the cell treatment apparatus 100 according to the present embodiment, the first region 1 and the second region 3 are configured by different housings, and the housings configuring the first region 1 and the second region 3 are placed adjacent to each other. However, the present invention is not limited to this, and the first region 1 and the second region 3 may be configured by a single housing with the first region 1 and the second region 3 divided within the housing. In the cell treatment apparatus 100 according to the present embodiment, the first region 1 and the second region 3 are configured by different housings. Thus, for example, each member in the cell treatment apparatus 100 can be maintained easily, and the cell treatment apparatus 100 can be assembled easily.

The first region 1 includes a work opening 11a on its front (frontward in FIG. 1) and a maintenance opening 11b for maintenance on its side. The opening 11a is a work opening for working on a cell treatment in the cell treatment chamber of the first region 1. The opening 11b is a maintenance opening through which the cell treatment chamber can be maintained. The area of the opening 11a is preferably smaller than that of the opening 11b, for example, because the maintenance operation is facilitated. The size and number of the openings 11a and 11b are not particularly limited, and reference can be made, for example, to the size and number of the work openings and the maintenance openings in the safety cabinet. As a specific example, for the size and number of the openings 11a and 11b, reference can be made, for example, to the safety cabinet standard specified in EN12469:2000, which is the EN standard. The number of the openings 11b is not particularly limited and can be any number, but is preferably 2 or more, for example, because maintenance becomes easier. The locations of the opening 11a and the opening 11b in the first region 1 are not particularly limited and may be any location. However, it is preferable that the opening 11a and the opening 11b are placed at different locations (e.g., different side surfaces) of the first region 1. In the present embodiment, the opening 11b is primarily intended to facilitate maintenance within the cell treatment apparatus 100, but may be used for other purposes. The cell treatment apparatus 100 according to the present embodiment, for example, enables observation of movement and the like of each of inside members through the opening 11b, thereby allowing direct observation of a defect site when a problem occurs in the cell treatment apparatus 100. Thus, countermeasures can be considered.

The wall in front of the first region 1 is a double wall having an outer wall and an inner wall, and the door 12a opens and closes the opening 11a by raising and lowering a rail placed in a space between the outer wall and the inner wall. The opening 11b can be opened and closed by detaching and attaching the door 12b covering the opening 11b. For example, when a cell treatment is performed in the cell treatment chamber, the opening 11b is preferably sealed with the door 12b. Thus, for example, the gas outside the cell treatment apparatus 100 and the dust contained in the gas outside the cell treatment apparatus 100 can be prevented from flowing into the cell treatment chamber. In the cell treatment apparatus 100 according to the present embodiment, the opening 11a and the door 12a thereof, and the opening 11b and the door 12b thereof may or may not have any configuration, and may include only any of the openings and the doors. However, the former is preferable because the size of the cell treatment apparatus 100 can be reduced by placing other members inside the double wall in the first region 1. When the wall of the first region 1 is a single wall, the door 12a is placed outside the first region 1, for example, like the door 12b. The type of opening and closing of the door is not particularly limited, and may be, for example, a lifting type such as the door 12a, an external type such as the door 12b, or another type. The other types include, for example, a double-door type, an accordion type, a pull door type, and the like. The material for forming the door is not particularly limited, and, for example, a material for forming each of the above-mentioned regions can be used, and a non-translucent material is preferable.

As shown in FIG. 2, the inner space of the first region 1 of the cell treatment apparatus 100 according to the present embodiment is a cell treatment chamber for treating cells and can be closed by closing the doors 12a and 12b, that is, can be opened and closed. The cell treatment chamber includes: an XY stage 13a and an arm 13b that are collectively a suction/discharge moving device; a suction/discharge device 14; a light source 15; a drainage container placement portion 16a; a storage container placement portion 17a; a culture vessel placement portion 18; and a collection container placement portion 19a. The XY stage 13a, the arm 13b, the suction/discharge device 14, the light source 15, the drainage container placement portion 16a, the storage container placement portion 17a, and the collection container placement portion 19a included in the cell treatment chamber are optional components in the present embodiment and may or may not be included, and one of them may be included, or two or more of them may be included. The XY stage 13a is placed on the bottom surface of the cell treatment chamber and is placed so as to be movable in the directions indicated by arrows X and Y. The arm 13b including a pair of arms is placed on the XY stage 13a. At the end of one of the arms in the arm 13b, the suction/discharge device 14 is placed with its suction/discharge port directed downward. Further, at the end of the other arm in the arm 13b, the light source 15 is placed so as to be able to emit light (perform light irradiation) in the downward direction. The drainage container placement portion 16a, the storage container placement portion 17a, the culture vessel placement portion 18, and the collection container placement portion 19a are placed on the bottom surface of the cell treatment chamber in this order along the moving direction of the XY stage 13a indicated by the arrow X. A drainage container 16b including a tip member detachment device 16c is placed in the drainage container placement portion 16a, a storage container 17b is placed in the storage container placement portion 17a, and a collection container 19b is placed in the collection container placement portion 19a.

The XY stage 13a and the arm 13b are provided as a suction/discharge moving device in the cell treatment apparatus 100 according to the present embodiment. However, the suction/discharge moving device is not limited thereto and may be capable of moving the suction/discharge device 14, and a known moving device can be used, for example. The moving direction of the suction/discharge moving device is not particularly limited, and the suction/discharge moving device may be, for example, movable in one direction (e.g., the direction indicated by the arrow Y), movable in two directions (e.g., the directions indicated by the arrows X and Y), or movable in three directions (e.g., the directions indicated by the arrows X, Y and Z). In the case of two directions, the first direction needs not to be parallel with the second direction and is preferably substantially orthogonal or orthogonal to the second direction. In this case, it is preferable that the plane including the first direction and the second direction is substantially parallel with the placement surface of the culture vessel placement portion 18. In the case of three directions, the third direction may intersect with, for example, a plane including the first direction and the second direction, and is preferably substantially orthogonal or orthogonal to the plane including the first direction and the second direction. In the present embodiment, the XY stage 13a is a known stage capable of moving an object at high speed and precisely along the directions indicated by the arrows X and Y via, for example, a linear motor cart or the like. The arm 13b is extendable in the vertical direction (the direction indicated by the arrow Z). However, the arm 13b may be fixed. In the latter case, the suction/discharge moving device is capable of moving the suction/discharge device 14 only on a plane substantially parallel with the bottom surface of the cell treatment chamber, i.e., only in the directions indicated by the arrows X and Y in FIG. 2.

The suction/discharge device 14 sucks and discharges, for example, a medium, cells, and the like in the cell culture vessel 184. The suction/discharge device 14 is used, for example, by attaching a tip member to be described later on the suction/discharge port side thereof. The suction/discharge device 14 is not particularly limited, and, for example, a known suction/discharge device can be used. Specific examples thereof include an electric pipette, an electric syringe pump, and the like.

The light source 15 emits light, for example, from the upper portion of the culture vessel placement portion 18 toward the culture vessel placement portion 18. The light source 15 is preferably used together when an optical microscope such as a phase-contrast microscope is used as the second imaging device to be described later, for example. The light emitted by the light source 15 is, for example, visible light. The light source 15 is not particularly limited, and examples thereof include known light sources such as a xenon light source, a light emitting diode (LED) illumination and a laser diode (LD). In the present embodiment, the light source 15 is placed on the arm 13b of the suction/discharge moving device and moves synchronously with the movement of the suction/discharge device 14. However, the light source 15 may move asynchronously with the suction/discharge device 14. As a specific example, the light source 15 may be placed in a light source moving device capable of moving the light source 15, which is different from the suction/discharge moving device, for example. In this case, the control device 51 to be described later may include a light source movement control unit that controls the movement of the light source moving device. As the moving direction of the light source moving device can be described with reference to the description of the moving direction of the suction/discharge device, for example.

The drainage container placement portion 16a is a region in which a drainage container 16b for draining a liquid sucked by the suction/discharge device 14 can be placed. The drainage container 16b placed in the drainage container placement portion 16a in the present embodiment is an optional component and may or may not be included. In the present embodiment, the drainage container 16b is a box having an upper opening, a wall on the storage container placement portion 17a side, extending upward, and a wall (upper surface) substantially parallel with the bottom surface of the cell treatment chamber, including a tip member detachment device 16c formed as a semicircular recess (notch) at the upper end thereof. The drainage container 16b can collect a tip member detached from the suction/discharge device 14. Thus, for example, the drainage container 16b can also be referred to as a tip member collection container, or the drainage container placement portion 16a can also be referred to as a tip member collection container placement portion. The tip member detachment device 16c is formed in a drainage container 16b and however may be placed separately. The tip member detachment device 16c may be placed in the vicinity of the suction/discharge device 14, specifically in the suction/discharge moving device in which the suction/discharge device 14 is placed.

The storage container placement portion 17a is a region in which the storage container 17b storing the tip member detachable from the suction/discharge device 14. The storage container 17b placed in the storage container placement portion 17a in the present embodiment is an optional component and may or may not be included. The tip member is not particularly limited, may be any member capable of storing the liquid sucked by the suction/discharge device 14 therein and can be, for example, a chip in the case where the suction/discharge device 14 is a pipette. The storage container 17b is, for example, a rack in which the chips are stored. The cell treatment apparatus 100 according to the present embodiment includes a tip member detachment device 16c and a storage container placement portion 17a, thereby simplifying (shortening) the movement of the cell culture vessel 184 when the medium, the cells, and the like inside the cell culture vessel 184 are sucked and discharged.

The collection container placement portion 19a is a region where a collection container 19b for collecting a suction liquid containing the cells collected by the suction/discharge device 14 can be placed. The collection container 19b placed in the collection container placement portion 19a in the present embodiment is an optional component and may or may not be included. Examples of the collection container 19b include culture vessels such as known dishes and known flasks.

In the present embodiment, on the bottom surface of the cell treatment chamber, the drainage container placement portion 16a, the storage container placement portion 17a, the culture vessel placement portion 18, and the collection container placement portion 19a are disposed in this order in the plane that is substantially parallel with the surface on which the culture vessel placement portion 18 is placed, i.e., the bottom surface of the cell treatment chamber along the direction of movement of an XY stage 13a in the long axis direction (direction indicated by the arrow X). However, each placement portion may not be placed along the long axis direction, and may not be placed in this order. In the present embodiment, the drainage container placement portion 16a, the storage container placement portion 17a, the culture vessel placement portion 18, and the collection container placement portion 19a are placed in the above-mentioned order. Thus, for example, the suction/discharge device 14 can move linearly, and the movement of the suction/discharge device 14 at the time of sucking and discharging the medium, the cells, and the like in the cell culture vessel 184 can be simplified (shortened).

As shown in FIG. 3, a first camera 20, illumination lamps 21a and 21b, and a germicidal lamp 22 are provided above the opening 11a in the front wall of the cell treatment chamber in the cell treatment apparatus 100 according to the present embodiment. The illumination lamps 21a and 21b are placed on both sides of the first camera 20 along the direction indicated by the arrow X, and the germicidal lamp 22 is placed above the first camera 20.

The camera 20 is provided as the first imaging device in the present embodiment. However, the first imaging device is an optional component and may or may not be included. The first imaging device is not limited to a camera and may be capable of taking an image of the inside of the cell treatment chamber. The first imaging device is not particularly limited, and a known imaging device such as a microscope or a camera or a combination of the known imaging device and a solid-state imaging element (image sensor) such as a CCD or a Complementary MOS (CMOS) can be used. In the present embodiment, the camera 20 is placed in the front wall inside the cell treatment chamber. However, the position of the camera 20 is not particularly limited, and the camera 20 may be placed at any position and preferably placed to allow taking of an image of a wide range within the cell treatment chamber. Specifically, in the case where the XY stage 13a and the arm 13b that are collectively a suction/discharge moving device and the suction/discharge device 14 are placed in back (the upper left side in FIG. 2) of the culture vessel placement portion 18 in the cell treatment chamber as in the cell treatment apparatus 100 according to the present embodiment, an image of a wide range within the cell treatment chamber can be taken. It is thus preferable to place them in front (the lower right side in FIG. 2) of the cell treatment chamber. It is preferable that the first imaging device is capable of taking an image at multiple magnifications (e.g., different magnifications). However, the first imaging device may be capable of taking an image at one magnification. The magnification means, for example, an imaging magnification. As a specific example, the camera 20 includes lenses with multiple magnifications (e.g., different magnifications). The first imaging device may be capable of optical zooming, digital zooming, or the like, for example. The cell treatment apparatus 100 according to the present embodiment includes a camera 20. Thus, for example, the operation inside the cell treatment chamber can be checked, and the reliability of the operation can be improved. The number of the first imaging devices placed inside the cell treatment chamber is not particularly limited, and may be one or more.

In the present embodiment, the illumination lamps 21a and 21b are provided as the illumination device. However, the illumination device is an optional component and may or may not be included. The illumination device is not limited to the illumination lamp and may be one capable of projecting light (illuminating) into the cell treatment chamber. The illumination device is not particularly limited, and, for example, a known illumination such as a fluorescent lamp or a light emitting diode (LED) lamp can be used. In the present embodiment, the illumination lamps 21a and 21b are placed on the front wall inside the cell treatment chamber. However, the positions of the illumination lamps 21a and 21b are not particularly limited and can be any positions, and are preferably placed such that they can be projected to a wide area within the cell treatment chamber, i.e., they are difficult to shade in the cell treatment chamber. Specifically, in the case where the XY stage 13a and the arm 13b that are collectively a suction/discharge moving device 13b and the suction/discharge device 14 are placed in back (the upper left side in FIG. 2) of the culture vessel placement portion 18 in the cell treatment chamber as in the cell treatment apparatus 100 according to the present embodiment, light can be transmitted over a wide range within the cell treatment chamber. It is thus preferable to place them in front (the lower right side in FIG. 2) of the cell treatment chamber. The cell treatment apparatus 100 according to the present embodiment includes the illumination lamps 21a and 21b. Thus, for example, the operation inside the cell treatment chamber can be checked, and the reliability of the operation can be improved. The number of the illumination devices placed in the cell treatment chamber is not particularly limited, and may be one or more.

In the present embodiment, a germicidal lamp 22 is provided as a germicidal device. However, the germicidal device is an optional component and may or may not be included. Moreover, the germicidal device is not limited to the germicidal lamp and may be capable of disinfecting the inside of the cell treatment chamber, specifically the periphery of the culture vessel placement portion 18. The germicidal device is not particularly limited, and for example, can be any of known germicidal devices such as a germicidal lamp and an ultraviolet LED lamp. In the present embodiment, the germicidal lamp 22 is placed on the front wall inside the cell treatment chamber. However, the position of the germicidal lamp 22 is not particularly limited and may be any position. For example, dust and the like outside the cell treatment apparatus 100 enter the openings 11a and 11b. It is thus preferable that the germicidal lamp 22 is placed to be capable of disinfecting the vicinities of the openings 11a and 11b. Specifically, in the case where an opening 11a is provided in the front wall of the cell treatment chamber as in the cell treatment apparatus 100 according to the present embodiment, the germicidal device is preferably placed above the opening 11a in the front wall of the cell treatment chamber. In the case where an opening 11b is provided in the wall on the side surface side of the cell treatment chamber as in the cell treatment apparatus 100 according to the present embodiment, the germicidal device is preferably placed above the opening 11b in the wall on the side surface side of the cell treatment chamber. When the cell treatment apparatus 100 includes the illumination device and the germicidal device, both of the devices are preferably placed on the same wall of the cell treatment chamber, for example, on a wall in which the opening 11a is provided. In this case, the germicidal device is provided preferably above the illumination device. The cell treatment apparatus 100 according to the present embodiment includes a germicidal lamp 22. Thus, for example, the cleanliness of the inside of the cell treatment chamber is improved. The number of germicidal devices placed in the cell treatment chamber is not particularly limited, and may be one or more.

In the first region 1 according to the present embodiment, as to the size, shape, structure, and the like of the cell treatment chamber, reference can be made to those of the safety cabinet, for example, and as a specific example, the standards of the safety cabinet specified in the above EN12469:2000.

As shown in FIGS. 4A and 4B, the culture vessel placement portion 18 in the cell treatment apparatus 100 according to the present embodiment includes an upper lid 181 and a bottom 182, and the upper lid 181 is detachably attached to the bottom 182. In the present embodiment, the culture vessel placement portion 18 is a box including the upper lid 181 and the bottom 182, and cell culture vessels 184 are placed inside the box. However, the culture vessel placement portion 18 is not limited to this, and cell culture vessels 184 may be placed in the culture vessel placement portion 18, the culture vessel placement portion 18 may be placed so as to be adjacent to the second region 3 in the cell treatment chamber, and the adjacent portion (bottom plate 186 in FIGS. 4A and 4B) of the culture vessel placement portion 18 to the second region 3 may be translucent. The "translucent" means, for example, transmission of the laser, the "translucent" that the laser emitted from the laser irradiation device 33 in the second region 3. Further, the case where the second region 3 includes a second imaging device to be described later means that the second imaging device can perform imaging via the bottom plate 186. A translucent region 183 is provided in the upper lid 181 such that the cell culture vessel 184 can be irradiated with light from the light source 15. The translucent region 183 is formed of, for example, a transparent glass plate, an acrylic plate, or the like. The bottom 182 includes a bottom wall 185 and a translucent bottom plate 186. The translucent bottom plate 186 is formed of, for example, a transparent glass plate, an acrylic plate, or the like. The bottom plate 186 is adjacent to the second region 3. For this reason, it can also be said that the adjacent portion of the culture vessel placement portion 18 to the second region 3, i.e., the bottom plate 186 forms a part of the wall of the cell treatment chamber. The contact portion between the bottom plate 186 and the wall of the cell treatment chamber is preferably sealed with a sealing member such as a gasket or a sealing material, for example. As a result, for example, the gas in the second region 3 and dust contained therein can be prevented from flowing into the culture vessel placement portion 18 and the cell treatment chamber. The bottom wall 185 includes four recesses 187 in which four cell culture vessels 184 can be respectively placed, and the side surface of each recess 187 has a reversely tapered shape that narrows from the inside of the cell treatment chamber toward the outside of the cell treatment chamber (from top toward bottom in FIG. 4B). Each recess 187 includes a projection 188 projecting toward the inside of the recess 187 on the end side of the bottom plate 186. The bottom end of the cell culture vessel 184 is in contact with the projection 188. In the cell treatment apparatus 100 according to the present embodiment, the bottom wall 185 has four recesses 187. However, the number of the recesses 187 in the bottom wall 185 is not limited to this, and can be appropriately set according to the number of the cell culture vessels 184 to be placed. The size of each recess 187 can be appropriately set in accordance with the size of the cell culture vessel 184 to be placed. In the culture vessel placement portion 18 according to the present embodiment, the recess 187 has the above-described structure. Thus, for example, the cell culture vessel 184 can be placed in the culture vessel placement portion 18 regardless of the shape of the side surface of the cell culture vessel 184. In the cell treatment apparatus 100 according to the present embodiment, the bottom wall 185 is integrally formed with the wall of the bottom surface and the wall of the side surface. However, the bottom wall 185 is not limited to this, and the wall of the bottom surface and the wall of the side surface may be different members. When the wall of the bottom surface and the wall of the side surface in the bottom wall 185 are configured by different members, for example, multiple walls of the bottom surfaces for the bottom wall 185, having different numbers and sizes of recesses 187 can be provided in advance. Thus, for example, the member of the wall of the bottom surface for the bottom wall 185 can be replaced with a member having a suitable number of recesses with suitable sizes for placement of the cell culture vessels 184 according to the size and number of the cell culture vessels 184.

The cell culture vessel 184 is not particularly limited, and examples thereof include culture vessels such as a well-known dish and flask used for cell culture. The material for forming the cell culture vessel 184 is not particularly limited and can be, for example, a material that transmits a laser beam emitted from the laser irradiation device 33 to be described later. Specific examples thereof include plastic, glass, and the like that transmit a laser beam. Examples of the plastic include polystyrene-based polymers, acrylic polymers (such as polymethyl methacrylate (PMMA)), polyvinylpyridine-based polymers (such as poly(4-vinylpyridine) and 4-vinylpyridine-styrene copolymers), silicone-based polymers (such as polydimethylsiloxane), polyolefin-based polymers (such as polyethylene, polypropylene, and polymethylpentene), polyester-based polymers (such as polyethylene terephthalate (PET) and polyethylene naphthalate (PEN)), polycarbonate-based polymers, and epoxy-based polymers.

The cell culture vessel 184 preferably includes, for example, a laser absorption layer formed of a polymer containing a dye structure (chromophore) for absorbing the laser or a photoacid generator for absorbing the laser and generating an acidic substance on a surface (lower side in FIGS. 4A and 4B) on which the laser beam is emitted from the laser irradiation device 33 to be described later. The dye structure and the photoacid generator can be described with reference to, for example, the description of Japanese Patent No. 6033980. The cell culture vessel 184 includes the laser absorption layer. Thus, for example, when a laser beam is emitted from the laser irradiation device 33 to be described later, the energy of the laser beam is converted into heat, acid, or the like, and the cells existing above the laser absorption layer can be killed, liberated, or the like.

The culture vessel placement portion 18 may further include, for example, a temperature adjustment device that adjusts the temperature of the cell culture vessel 184. When the culture vessel placement portion 18 includes the temperature adjustment device, the culture conditions during the treatment of the cells in the cell culture vessel 184 can be kept constant, and for example, damage to the cells at the time of the treatment of the cells can be reduced. The temperature adjustment device may be, for example, a heating device such as a heater.

The culture vessel placement portion 18 may further include, for example, pH adjustment device that adjusts the pH of the culture medium in the cell culture vessel 184. When the culture vessel placement portion 18 includes the pH adjustment device, the culture conditions during the treatment of the cells in the cell culture vessel 184 can be kept constant, and for example, damage to the cells at the time of the treatment of the cells can be reduced. Examples of the pH adjustment device include a carbon dioxide cylinder and a carbon dioxide concentration adjustment device. The pH adjustment device can be, for example, specifically a connector connected to a carbon dioxide supply device outside the cell treatment apparatus 100.

As shown in FIGS. 5 and 6, in the cell treatment apparatus 100 according to the present embodiment, the circulator 7 includes an intake unit 71, circulation path 72, a gas supply unit 73, and an discharge unit 74. Thus, the circulator 7 circulates the gas in the cell treatment chamber.

The intake unit 71 intakes the gas in the cell treatment chamber. The intake unit 71 may intake gas outside the cell treatment apparatus 100 instead of or in addition to the gas in the cell treatment chamber. In the present embodiment, the intake unit 71 is placed in the vicinity of (e.g., directly below) the opening 11a of the cell treatment chamber. Specifically, the intake unit 71 has multiple openings (e.g., slits) formed on its upper surface (not shown) and is placed below the opening 11a such that the opening communicates with the opening 11a. By placing the intake unit 71 in the vicinity of the opening 11a of the cell treatment chamber as described above, for example, the gas outside the cell treatment apparatus 100 and the dust and the like contained therein can be prevented from flowing into the cell treatment chamber at the time when the operator opens the door 12a and works in the cell treatment chamber. The intake unit 71 may be placed in the vicinity of the opening 11b instead of or in addition to the opening 11a. The intake unit 71 may intake the gas in the cell treatment chamber with a blowing device such as a fan, for example.

The circulation path 72 connects the intake unit 71 with the gas supply unit 73 and the discharge unit 74. In the present embodiment, the circulation path 72 is placed in a space between the outer wall and the inner wall and in an upper portion of the first region 1. The circulation path 72 is, for example, a hollow tube. One end of the circulation path 72 communicates with the intake unit 71, and the other end communicates with the gas supply unit 73 and the discharge unit 74. When the circulation path 72 is placed in a space between the outer wall and the inner wall as in the cell treatment apparatus 100 according to the present embodiment, for example, the size of the cell treatment apparatus 100 can be reduced. In the present embodiment, the circulator 7 includes the circulation path 72. However, the circulation path 72 may or may not be included. In the latter case, the intake unit 71 is connected to, for example, directly the gas supply unit 73 and the discharge unit 74. The circulation path 72 may blow the gas taken in by the intake unit 71 to the gas supply unit 73 and the discharge unit 74 with a blowing device such as a fan, for example.

When the circulation path 72 includes the blowing device, the blowing device may be placed in the vicinity of the intake unit 71, the gas supply unit 73, or the discharge unit 74, or may be placed in any of other positions such as the central portion thereof. However, it is preferable to place the blowing device in the vicinity of the intake unit 71 because, the intake from the intake unit 71 is improved, and the dust and the like can be effectively prevented from flowing into the cell treatment chamber, for example, as compared with the downflow generated by the gas supply unit 73 to be described later. When the blowing device is placed in the vicinity of the intake unit 71, it is preferable that the blowing device is placed in, for example, the second region 3 or the third region 5. As a specific example, when the circulation path 72 further includes the blowing device in the cell treatment apparatus 100 according to the present embodiment, the blowing device is placed in front (the lower left side in FIG. 1), that is, on the lower side of the intake unit 71 in the second region 3 or the third region 5. In this case, the circulation path 72 connects the intake unit 71 with the intake side of the blowing device and connects the blowing side of the blowing device with the gas supply unit 73 and the discharge unit 74. That is, the circulation path 72 is placed in the second region 3 or the second region 3 and the third region 5, the space between the outer wall and the inner wall, and the upper portion of the first region 1.

The gas supply unit 73 supplies a part of the gas taken in by the intake unit 71 into the cell treatment chamber. In the present embodiment, the gas supply unit 73 communicates with the upper end of the first region 1 such that the gas taken in by the intake unit 71 can be supplied into the cell treatment chamber. The gas supply unit 73 may supply the gas into the cell treatment chamber by the blowing device such as a fan, for example. The gas supply unit 73 may include, for example, a gas purification member. In this case, the gas supplied from the gas supply unit 73 into the cell treatment chamber passes through the gas purification member. When the gas supply unit 73 includes the gas purification member, for example, the dust or the like can be prevented from flowing into the cell treatment chamber. Examples of the gas purification member include a filter for collecting fine particulates such as a high efficiency particulate air filter (HEPA filter and an ultra-low penetration air filter (ULPA filter). In the cell treatment apparatus 100 according to the present embodiment, the upper part of the cell treatment chamber is connected to the gas supply unit 73. Thus, for example, blowing air from the gas supply unit 73 causes downflow, which can more effectively prevent dust from flowing into the cell treatment chamber from the opening 11a.

The discharge unit 74 discharges the remainder of the gas taken in by the intake unit 71 to the outside of the cell treatment chamber, specifically, to the outside of the cell treatment apparatus 100. In the present embodiment, the discharge unit 74 is placed at an upper end (topmost portion) of the cell treatment apparatus 100 such that the gas taken in by the intake unit 71 can be discharged to the outside of the cell treatment apparatus 100. When the discharge unit 74 is provided in the topmost portion of the cell treatment apparatus 100 in this manner, for example, the size of the cell treatment apparatus 100 can be reduced, and the dust stirred up due to discharge can be prevented from flowing into the cell treatment chamber. The discharge unit 74 may discharge the gas to the outside of the cell treatment apparatus 100 with a blowing device such as a fan, for example. The discharge unit 74 may include, for example, a gas purification member. In this case, the gas discharged from the discharge unit 74 to the outside of the cell treatment apparatus 100 passes through the gas purification member. When the discharge unit 74 includes a gas purification member, for example, fine particles or the like generated in the cell treatment chamber can be prevented from blowing out of the cell treatment apparatus 100.

In the circulator 7 according to the present embodiment, as to the size, shape, structure, and the like of each part, reference can be made to those of the safety cabinet, for example, and as a specific example, reference can be made to the standard of the safety cabinet specified in the above-mentioned EN12469:2000.

As shown in FIG. 7A, in the cell treatment apparatus 100 according to the present embodiment, the second region 3 includes a second XY stage 31, a microscope 32 having objective lenses 321a to 321c with three different magnifications, and a laser irradiation device 33. The XY stage 31 and the microscope 32 included in the cell treatment apparatus 100 according to the present embodiment are optional components and may or may not be included, and one of them may be included. The XY stage 31 is placed on the placement surface of the culture vessel placement portion 18, that is, on the bottom surface of the second region 3 substantially parallel with the bottom surface of the cell treatment chamber. On a common rail (moving path) in the direction indicated by the arrow Y in the XY stage 31, two rails in the direction indicated by the arrow X are placed so as to be movable on the common rail.

Carriages 311a and 311b are placed on the respective rails in the direction indicated by the arrow X so as to be movable on the respective rails. The laser irradiation device 33 includes a laser light source 331, a laser emission unit 332, and an optical fiber 333. At the upper part of the XY stage 31, the microscope 32 is placed on the carriage 311b such that the objective lenses 321a to 321c face upward (the direction indicated by the arrow Z), and the laser emission unit 332 of the laser irradiation device 33 is placed on the carriage 311a such that a laser emission port face upward (the direction indicated by the arrow Z). The carriage 311a is movable up and down in the vertical direction (the direction indicated by the arrow Z). By the movement, a spot diameter formed in a portion to be irradiated with the laser in an object to be irradiated can be adjusted. The laser light source 331 is placed on the bottom surface of the second region 3 in a region which does not overlap with the movable range of the XY stage 31 in the second region 3. One end of the optical fiber 333 is connected to the laser light source 331, and the other end is connected to the laser emission unit 332.

The XY stage 31 is provided as a laser moving device and a second imaging moving device in the cell treatment apparatus 100 according to the present embodiment. However, the laser moving device and the second imaging moving device are not limited to this and may be capable of moving the laser irradiation device 33 and a second imaging device to be described later, and for example, a known moving device can be used. In the present embodiment, the laser moving device and the second imaging moving device share a rail in the direction indicated by the arrow (first direction). However, the laser moving device and the second imaging moving device may be independent. As a specific example, as shown in FIG. 7B, on the bottom surface of the second region 3, the laser moving device may be placed as, for example, an XY stage 31a, and the second imaging moving device may be placed as an XY stage 31b. The moving directions for the laser moving device and the second imaging moving device are not particularly limited, and they may be, for example, movable in one direction (for example, the direction indicated by the arrow Y), movable in two directions (for example, the directions indicated by the arrows X and Y), or movable in three directions (for example, the directions indicated by the arrows X, Y and Z). In the case of two directions, the first direction needs not to be parallel with the second direction and is preferably substantially orthogonal or orthogonal to the second direction. In this case, it is preferable that the plane including the first direction and the second direction is substantially parallel with the placement surface of the culture vessel placement portion 18. In the case of three directions, the third direction may intersect with, for example, a plane including the first direction and the second direction, and is preferably substantially orthogonal or orthogonal to the plane including the first direction and the second direction. When the laser moving device is capable of moving the laser irradiation device 33 in the direction substantially orthogonal to the placement surface of the culture vessel placement portion 18, i.e., the bottom surface of the cell culture vessel 184, the laser moving device is capable of adjusting the spot diameter to be described later, for example. In this case, the laser moving device also serves as, for example, a spot diameter adjustment device to be described later. In the present embodiment, the XY stage 31 is a known stage capable of moving an object at high speed and precisely along the directions indicated by the arrows X and Y via, for example, a linear motor carriage or the like.

It is preferable that the laser moving device and the second imaging moving device are capable of moving the laser irradiation device 33 and the second imaging moving device in the first direction (for example, the direction indicated by the arrow Y in FIG. 7A) on a plane substantially parallel to the placement surface of the culture vessel placement portion 18, respectively, as in the XY stage 31 according to the present embodiment, and that the movement of the laser irradiation device 33 by the laser moving device in the first direction and the movement of the second imaging device by the second imaging moving device in the first direction are on the same straight line. When the laser irradiation device 33 and the second imaging device move on the same straight line in this manner, the number of times of movement of each device can be reduced, and the treatment time can be reduced, in the cell treatment performed by the laser irradiation device 33 after taking an image of the cells in the cell culture vessel 184 by the second imaging device, for example. Further, as in the XY stage 31 according to the present embodiment, it is preferable that the laser moving device includes a carriage 311a in which the laser irradiation device 33 is placed and a moving path (rail) in which the carriage 311a moves and which is placed along the first direction, and that the second imaging moving device includes a carriage 311b in which the second imaging device is placed and a moving path (rail) in which the carriage 311b moves and which is placed along the first direction, and that the moving path of the laser moving device is the same as that of the second imaging device. With this configuration, it is possible to further reduce the number of times of movement of each device and the treatment time in the cell treatment performed by the laser irradiation device 33 after imaging by the second imaging device.

A microscope 32 having objective lenses 321a to 321c with three different magnifications is provided as the second imaging device in the cell treatment apparatus 100 according to the present embodiment. However, the second imaging device is not limited to this and may be capable of taking an image of cells in the cell culture vessel 184 placed in the culture vessel placement portion 18. The second imaging device is not particularly limited, and a known imaging device such as a microscope or a camera or a combination of the known imaging device and a solid-state imaging element (image sensor) such as a CCD or a Complementary MOS (CMOS) can be used. Examples of the microscope include optical microscopes such as a phase-contrast microscope and a fluorescence microscope. The microscope may have, for example, both functions of the phase-contrast microscope and the fluorescence microscope. The second imaging device is preferably capable of taking an image at multiple magnifications, for example, and may however be capable of taking an image at one magnification. As a specific example, when the second imaging device is a microscope, it is preferable that the microscope has objective lenses with multiple magnifications (for example, different magnifications). In the present embodiment, the magnifications of the objective lenses 321a to 321c are, for example, 2, 4 and 8 times, respectively. The second imaging device may be capable of optical zooming, digital zooming, or the like, for example. When the first imaging device and the second imaging device are included as in the cell treatment apparatus 100 according to the present embodiment, the magnification of the second imaging device is preferably higher than that of the first imaging device because an image of cells in the cell culture vessel 184 can be taken more clearly.

In the cell treatment apparatus 100 according to the present embodiment, the laser irradiation device 33 includes a laser light source 331, a laser emission unit 332, and an optical fiber 333. However, the laser irradiation device 33 is not limited to this and may be capable of irradiating the cell culture vessel 184 placed in the culture vessel placement portion 18 with a laser. The laser irradiation device 33 may include, for example, a laser light source 331, and the laser light source 331 may directly irradiate the cell culture vessel 184 with a laser. When the laser from the laser light source 331 is guided to the laser emission unit 332, laser may be guided using a light guide unit such as a mirror and micro electro mechanical systems (MEMS) instead of the optical fiber 333. However, the optical fiber 333 is preferable because the laser light source 331 can be placed at any position in the second region 3, and for example, by placing the laser light source 331 in a region in which other devices such as the laser moving device, the second imaging device, and the second imaging moving device are not placed and which does not overlap with the movable range of the other devices, the size of the cell treatment apparatus 100 can be reduced, and the weight of the cell treatment apparatus 100 can be reduced as compared with the case of using other light guide units.

The laser light source 331 is, for example, a device that oscillates a continuous-wave laser or a pulsed laser. The laser light source 331 may be, for example, a high-frequency laser having a long pulse width close to a continuous wave. The output of the laser oscillated from the laser light source 331 is not particularly limited, and can be appropriately determined depending on, for example, treatment and cells. The wavelength of the laser oscillated by the laser light source 331 is not particularly limited, and can be, for example, a visible light laser of 405 nm, 450 nm, 520 nm, 532 nm, 808 nm, or the like, an infrared laser, or the like. As mentioned above, in the case where the cell culture vessel 184 is provided with a laser absorption layer, the laser light source 331 oscillates, for example, a laser of a wavelength that can be absorbed by the laser absorption layer. It is preferable that the laser light source 331 oscillates a laser with a wavelength greater than 380 nm to prevent influence on cells. As a specific example, the laser light source 331 may be a continuous-wave diode laser with a maximum-power of 5 W and a wavelength near 405 nm.

When the laser irradiation device 33 includes a laser emission unit 332, it is preferable that the laser moving device moves the laser emission unit 332. When the laser moving device moves the laser emission unit 332 in the vertical direction (the direction indicated by the arrow Z in FIGS. 7A and 7B), it is preferable to move the laser emission unit 332 such that the laser emission port of the laser emission unit 332 does not come into contact with the bottom surface of the cell treatment chamber, preferably the bottom surface of the culture vessel placement portion 18. As a specific example, it is preferable that the laser moving device moves the laser emission port of the laser emission unit 332 so as not to approach within 1 mm relative to the bottom surface of the culture vessel placement portion 18. When the laser moving device moves the laser emission unit 332 in such a range, for example, it is possible to prevent sway of the culture medium in the cell culture vessel 184 placed in the culture vessel placement portion 18 caused by contact between the laser emission unit 332 and the bottom surface of the culture vessel placement portion 18.

In the present embodiment, the microscope 32, which is the second imaging device, is placed in front (the lower left side in FIGS. 7A and 7B), and the laser irradiation device 33 is placed in back (the upper right side in FIGS. 7A and 7B). However, the positional relationship between the second imaging device and the laser irradiation device 33 is not limited to this, and for example, the second imaging device may be placed in back and the laser irradiation device 33 may be placed in front. Generally, the volume of the second imaging device such as a microscope is larger than that of the laser irradiation device 33. Thus, in the case where the culture vessel placement portion 18 is placed in front of the first region 1, the size of the cell treatment apparatus 100 can be reduced by placing the second imaging device in back and placing the laser irradiation device 33 in front.

The cell treatment apparatus 100 according to the present embodiment may further include a carriage 311a that can be raised/lowered as the spot diameter adjustment device. However, the spot diameter adjustment device is not limited to this and may be any device capable of adjusting the spot diameter formed in a portion to be irradiated (e.g., the bottom surface of the cell culture vessel 184) in an object to be irradiated by a laser. The spot diameter means a diameter of a laser beam at a contact portion between the laser and the object to be irradiated. In the present embodiment, the spot diameter is adjusted by raising or lowering the carriage 311a, i.e., by moving the carriage 311a in the direction indicated by the arrow Z to change the distance between the laser irradiation device 33 and the bottom surface of the cell culture vessel 184, which is the object to be irradiated. The distance between the laser irradiation device 33 and the object to be irradiated means, for example, a distance in a direction substantially orthogonal to the placement surface of the culture vessel placement portion 18, that is, the bottom surface of the cell culture vessel 184. In the case where the laser irradiation device 33 includes the laser emission unit 332, the distance between the laser irradiation device 33 and the object to be irradiated means a distance between the laser emission unit 332 and the object to be irradiated. The present invention, however, is not limited to this, and the spot diameter may be adjusted by switching the lens of the laser irradiation device 33. In the case where the spot diameter is adjusted by switching the lens, for example, it is preferable that the laser irradiation device 33 includes, for example, multiple lenses, and the spot diameter adjustment device adjusts the spot diameter by switching the lens. The multiple lenses may be, for example, multiple laser condensing lenses, multiple collimator lenses, or a combination of one or more condensing lenses and one or more collimator lenses. The multiple condensing lenses have different focal lengths, for example. The multiple collimator lenses have different focal lengths, for example. The lens may be switched manually, for example, or may be switched by a spot diameter adjustment control unit to be described later. In the latter case, for example, the spot diameter adjustment control unit includes a lens switching unit, and the lens is switched by the lens switching unit. The spot diameter adjustment device adjusts the spot diameter to be small, for example, when division of a cell mass, excision of cells or a cell mass in a specific region, killing of specific cells, and the like are performed in the case of performing a cell treatment in which a small spot diameter is desired. The spot diameter adjustment device adjusts the spot diameter to be large, for example, when cells in a specific region are caused to be dead in the case of performing a cell treatment in which a large spot diameter is to be killed. The size of the spot diameter is not particularly limited, and can be appropriately set according to, for example, the type of the cell treatment, the size of the cells, and the like.

In the cell treatment apparatus 100 according to the present embodiment, it is preferable that the movement of the gas between the cell treatment chamber and the second region 3 is prevented. The movement of the gas can be prevented, for example, by sealing an adjacent portion to the second region 3 in the cell treatment chamber with a sealing member such as the above-mentioned gasket and a sealing material. When the movement of the gas is prevented in this manner, for example, dust contained in the gas can be prevented from flowing into the cell treatment chamber.

In the cell treatment apparatus 100 according to the present embodiment, the third region 5 includes a control device 51 and a power supply device 52. As shown in FIG. 8, the control device 51 includes a configuration similar to a personal computer, a server computer, a workstation, or the like. As shown in FIG. 8, the control device 51 includes a central processing unit (CPU) 51a, a main memory 51b, an auxiliary storage device 51c, a video codec 51d, an I/O interface 51e, and the like, which are controlled by a controller (a system controller, an I/O controller, and the like) 51*f* and operate in cooperation with each other. The auxiliary storage device 51*c* can be a storage device such as a flash memory and a hard disc drive. The video codec 51*d* includes: a graphics processing unit (GPU) that generates a screen to be displayed based on a drawing instruction received from the CPU 51*a* and transmits signals of the screen to a display device or the like outside the cell treatment apparatus 100; and a video memory that temporarily stores the screen and image data, for example. The input-output (I/O) interface 51*e* is a device that is communicably connected to and controls a first XY stage 13*a* and an arm 13*b* (suction/discharge moving device), a suction/discharge device 14, a camera 20 (first imaging device), a second XY stage 31 (laser moving device, second imaging moving device) a microscope 32 (second imaging device), a laser irradiation device 33, and the like. The I/O interface 51*e* may include a servo driver (servo controller). The I/O interface 51*e* may be connected to an input device outside the cell treatment apparatus 100, for example. Examples of the display device include a monitor (for example, various image display devices such as a liquid crystal display (LCD) and a cathode ray tube (CRT) display) which output images. Examples of the input device 8 include a touch panel, a track pad, and a pointing device such as a mouse, a keyboard, and a push button which can be operated by a finger of a user.

The program executed by the control device 51 is stored in the auxiliary storage device 51*c*. The program is read into the main memory 51*b* at the time of executing the program and is decoded by the CPU 51*a*. The control device 51 controls each member according to the program.

The laser control unit, the suction/discharge control unit, the first imaging control unit, the second imaging control unit, and the spot diameter adjustment control unit included in the control device 51 in the present embodiment are optional components and may or may not be included. When the control device 51 has functions of the laser control unit, the suction/discharge control unit, the first imaging control unit, the second imaging control unit, and the spot diameter adjustment control unit in the cell treatment apparatus 100 according to the present embodiment, for example, each member is not required to be provided with a control unit, and the size of the cell treatment apparatus can be reduced. The present invention, however, is not limited to this, and for example, a control device may be provided in each member, and the control device 51 and the control device of each member may cooperate to control each member in order to reduce the load on the control device 51. As a specific example, the laser oscillation or the like may be controlled by, for example, a control device provided in each member, and the laser irradiation device 33 may be controlled by, for example, the control device 51. In addition, the control device 51 may be configured by one semiconductor element, a chip in which multiple semiconductor elements are packaged in one package, or a configuration in which multiple semiconductor elements are provided on a substrate.

In the present embodiment, the laser control unit controls the laser irradiation performed by the laser irradiation device 33 and the movement of the laser emission unit 332 of the laser irradiation device 33 performed by the XY stage 31 and the carriage 311*a*, which are the laser moving device. However, the laser control unit may control either one of them.

In the present embodiment, the suction/discharge control unit controls suction/discharge performed by the suction/discharge device 14 and the movement of the suction/discharge device 14 performed by the XY stage 13*a* and the arm 13*b*, which are the suction/discharge moving device. However, the suction/discharge control unit may control either one of them.

In the present embodiment, the first imaging control unit controls taking an image of the inside of the cell treatment chamber performed by the camera 20 which is the first imaging device.

In the present embodiment, the second imaging control unit controls the taking of an image of the cells performed by the microscope 32, which is the second imaging device, and the movement of the microscope 32 performed by the XY stage 31 and the carriage 311*b*, which are the second imaging moving device. However, the second imaging control unit may control either one of them.

In the present embodiment, the spot diameter adjustment control unit controls raising/lowering of the carriage 311*a* that is the spot diameter adjustment device. However, the spot diameter adjustment control device may control the adjustment of the spot diameter performed by the spot diameter adjustment control unit. In the case where the lens is switched manually as mentioned above, the spot diameter adjustment control unit may not be included.

The power supply device 52 is not particularly limited, and a known power supply can be used. The power supply device 52 supplies electric power to members (devices) activated by electric power, such as the laser irradiation device 33, the laser moving device, the first imaging device, the second imaging device, the second imaging moving device, the suction/discharge device 14, the suction/discharge moving device, the circulator 7, the illumination device, the germicidal device, the control device 51, and the like, for example. Thus, the power supply device 52 is electrically connected to, for example, the members (device) activated by electric power. The power supply device 52 supplies electric power at a voltage of, for example, 100 V. This enables the cell treatment apparatus 100 to be used even in a general electric power environment, for example. In the cell treatment apparatus 100 according to the present embodiment, the power supply device 52 is responsible for the entire power supply, and a power supply device is not required to be provided individually for each member. Thus, for example, the size and the weight of the cell treatment apparatus 100 can be reduced. However, the present invention is not limited to this, and, for example, a dedicated power supply device may be provided for at least one of the devices.

A communication device (not shown) may further be provided in the third region 5 of the cell treatment apparatus 100 according to the present embodiment. The communication device has a function of transmitting/receiving data to/from an external device such as a personal computer, a mobile communication device, or the like, or a function of connecting to the Internet or the like, for example, by wire or wireless communication. The communication unit may be, for example, an existing communication module or the like. When a communication device is provided in this manner, the cell treatment apparatus 100 can be connected to the outside. Thus, the cell treatment apparatus 100 can be operated from the outside or can receive data from the outside, for example. In addition, data in the cell treatment apparatus 100 can be browsed by, for example, connecting from the outside.

Next, treatment of cells and collection of treated cells using the cell treatment apparatus 100 according to the present embodiment will be described by way of example.

First, a germicidal lamp 22 is turned off, and illumination lamps 21*a* and 21*b* are turned on. In addition, a camera 20 is activated by the first imaging control unit to start taking an image of the inside of a cell treatment chamber. The image of the inside of the cell treatment chamber taken by the camera 20 is output to a display device via, for example, a control device 51. Further, a circulator 7 is activated to circulate the gas in the cell treatment chamber. Thereafter, an operator opens a door 12a of the opening 11a, places a cell culture vessel 184 in a culture vessel placement portion 18, and places a collection container 19b in a collection container placement portion 19a. A laser absorption layer is formed on the bottom surface of the cell culture vessel 184. After the placement, the operator closes the door 12a of the opening 11a.

Next, a second imaging control unit controls a XY stage 31 and a carriage 311b to move, thereby moving a microscope 32 to the lower side of the bottom surface of the cell culture vessel 184. Further, the suction/discharge control unit controls a XY stage 13a to move, thereby moving the light source 15 to the upper portion of the upper surface of the cell culture vessel 184, that is, to the upper portion of the culture vessel placement portion 18. Then, the microscope 32 takes an image of the cells in the cell culture vessel 184. Taking an image by the microscope 32 is performed multiple times, for example, using objective lenses 321a to 321c with different magnifications depending on the size of the cells to be treated. The image taken by the microscope 32 includes, for example, a phase contrast microscope image taken by a phase-contrast microscope, a fluorescence microscope image taken by a fluorescence microscope, and the like. The taken image is output to the display device via, for example, the control device 51.

For example, when the operator designates a region of cells to be treated (e.g., a region of cells to be collected) by the input device based on the taken image, the laser control unit controls an XY stage 31 and a carriage 311a to move. The laser emission unit 332 is moved to a position where cells surrounding a region of cells to be treated can be irradiated with a laser under the bottom surface of the cell culture vessel 184. The laser control unit controls the laser light source 331 to oscillate a laser. The oscillated laser is guided by the optical fiber 333 and irradiated from the laser emission unit 332. Further, with the laser irradiation, the XY stage 31 and the carriage 311a are moved around the cells to be treated by the laser control unit. At this time, the size of the spot diameter is adjusted to an appropriate size by moving the carriage 311a up and down in accordance with the size of the cells surrounding the region of the cells to be treated so as not to affect the cells in the region of the cells to be treated. The irradiated laser is absorbed by the laser absorption layer formed on the bottom surface of the cell culture vessel 184, and cells surrounding the cells to be treated are killed by heat or the like generated from the laser absorption layer. This makes it possible to excise the region of cells to be treated.

Next, the suction/discharge control unit controls the XY stage 13a to move, thereby moving the suction/discharge device 14 to the upper portion of the storage container 17b. The suction/discharge control unit controls the arm 13b to move up and down, thereby attaching a chip, which is the tip member, to the suction/discharge port side of the suction/discharge device 14. Next, the suction/discharge control unit controls the XY stage 13a to move, thereby moving the suction/discharge device 14 to the upper portion of the region of cells to be treated in the upper portion of the cell culture vessel 184. The suction/discharge control unit controls the arm 13b to move down, thereby placing the opening of the chip in the vicinity of the region of cells to be treated.

In this state, the suction/discharge control unit controls the suction/discharge device 14 to suck the cells in the region of cells to be treated together with the surrounding medium into the chip.

Further, the suction/discharge control unit controls the arm 13b to move up and the XY stage 13a to move, thereby moving the suction/discharge device 14 to the upper portion of the collection container 19b. Further, the suction/discharge control unit controls the arm 13b to move down, thereby moving the opening of the chip to the inside of the collection container 19b. In this state, the suction/discharge control unit controls the suction/discharge device 14 to discharge the medium containing the cells in the region of cells to be treated in the chip into the collection container 19b.

After the discharge, the suction/discharge control unit controls the arm 13b to move up and the XY stage 13a to move, thereby moving the suction/discharge device 14 to the upper portion of the drainage container 16b. Further, the suction/discharge control unit controls the arm 13b to move down and the XY stage 13a to move, thereby catching the upper end of the chip by the tip member detachment device 16c, which is a recess in the upper surface provided in the drainage container 16b. In this state, the suction/discharge control unit controls the arm 13b to move up, thereby detaching the chip from the suction/discharge device 14.

Then, the operator opens the door 12a of the opening 11a, collects the cell culture vessel 184 from the culture vessel placement portion 18, and collects the collection container 19b from the collection container placement portion 19a. In this manner, the cell treatment apparatus 100 according to the present embodiment can perform a cell treatment and collect the treated cells.

The cell treatment apparatus 100 according to the present embodiment is capable of easily subjecting cells in the cell culture vessel 184 to treatments such as screening and collecting, for example. In addition, the cell treatment apparatus 100 according to the present embodiment is not affected by the skill level of the operator, for example because cells are treated not by the operator himself but by the laser irradiation device. Thus, for example, the quality of the cells obtained after the treatment is stabilized. When the cell treatment apparatus 100 according to the present embodiment includes a spot diameter adjustment device, for example, the spot diameter can be adjusted to an appropriate size by the treatment performed on cells, and the cell treatment can be performed quickly. The adjustment of the spot diameter to an appropriate size allows the influence on cells not to be subjected to the treatment to be reduced, for example.

Next, the method for treating an object to be treated according to the present invention will be described by way of example.

As mentioned above, the method for treating an object to be treated according to the present invention includes: a cutting step of, in an object to be treated including a light-absorbing layer and a culture existing above the light-absorbing layer, irradiating the light-absorbing layer corresponding to a region to be cut in the culture with light to cut the culture existing above the light-absorbing layer into a predetermined shape; and a treating step of irradiating the light-absorbing layer corresponding to a portion other than the region to be cut with light to subject the culture existing above the light-absorbing layer to a killing treatment, and a first spot diameter formed in a portion to be irradiated with the light in the light-absorbing layer by the light in the cutting step is different from the second spot diameter formed in a portion to be irradiated in the light-absorbing layer by the light in the treating step.

In the treatment method according to the present invention, the first spot diameter is different from the second spot diameter, and other steps and conditions are not particularly limited. In the treatment method according to the present invention, the first spot diameter is different from the second spot diameter. Thus, for example, the first spot diameter and the second spot diameter can be appropriate spot diameters suitable for the cutting and the killing treatment. Therefore, by the treatment method according to the present invention, the cutting step can be performed with a spot diameter suitable for the cutting, and the treating step can be performed with a spot diameter suitable for the killing treatment. Accordingly, for example, operability is improved, thereby allowing the treatment time to be shortened. The treatment method according to the present invention can be described, for example, with reference to the cell treatment apparatus according to the present invention. The treatment method according to the present invention can be performed using, for example, the cell treatment apparatus according to the present invention. In the case where the treatment method according to the present invention is performed using the cell treatment apparatus according to the present invention, the treatment method can be described with reference to the description of the cell treatment apparatus by reading "laser" as "light" and reading "object to be irradiated" to "light-absorbing layer".

The culture is not particularly limited, and examples thereof include a cell, a bacteria, and fungus. The cell is not particularly limited and may be a cell mass composed of cells, a tissue, an organ, or the like, for example. The cell may be, for example, a cultured cell or a cell isolated from a living body. The cell mass, tissue, or organ may be, for example, a cell mass, tissue, or organ produced from the cell, or may be a cell mass, tissue, or organ isolated from a living body.

The light-absorbing layer is a layer containing a light-responsive substance. Examples of the light-responsive substance include a polymer containing a dye structure (chromophore) for absorbing light and a photoacid generator for absorbing light and generating an acidic substance. For example, a known polymer can be used as the former, and a photoacid generator can be used as the latter. In the case where the light is laser, the light-responsive substance can be described with reference to, for example, the descriptions of the polymer containing a dye structure for absorbing laser and the photoacid generator for absorbing laser and generating an acidic substance. In the case where the light-absorbing layer contains the light-responsive substance, for example, when light irradiation is performed by the light irradiation device, the energy of the light is converted into heat, acid, or the like, and the culture existing above the laser-absorbing layer can be killed, liberated, or the like.

The culture may be present above the light-absorbing layer and may be in direct or indirect contact with the light-absorbing layer, for example. In the latter case, for example, an anchorage such as an extracellular matrix is laminated on the light-absorbing layer, and the culture is in direct contact with the anchorage.

The cutting step is a step of irradiating the light-absorbing layer corresponding to a region to be cut in the culture with light to cut the culture existing above the light-absorbing layer into a predetermined shape. As mentioned above, the light irradiation layer contains the light-responsive substance. Thus, the light-absorbing layer irradiated with light generates, for example, heat, acid, and the like, and as a result, the culture corresponding to the light-absorbing layer can be killed, liberated, or the like. The cutting step can be performed by moving a light irradiation position for the light-absorbing layer corresponding to the region to be cut such that the culture can be cut into a predetermined shape, for example. The light irradiation can be performed, for example, by guiding light oscillated from the light source to the light-absorbing layer using a known light source. The wavelength of the light with which the light-responsive substance is irradiated is not particularly limited and can be determined, as appropriate, according to the kind of the light-responsive substance contained in the light-absorbing layer, for example. The light may be, for example, light having a wavelength distribution and is preferably light of a single wavelength, i.e., laser. When the light is laser, for example, the first spot diameter can be accurately controlled, and more accurate cutting can be performed. The wavelength of the laser is not particularly limited and can be described with reference to the description of the above-mentioned wavelength of the laser, for example. The light is preferably a light beam. The light source is not particularly limited, can be determined, as appropriate, according to the wavelength, and the kind of the light and can be described with reference to the description of the above-mentioned light source, for example. In the case where the light is laser, the light source can be, for example, the laser light source.

The cut shape of the culture is not particularly limited, and examples thereof include: circular shapes such as a circle, an exact circle, and an ellipse; a semicircular shape; and polygonal shapes such as a triangle, a quadrangle, a square, and a rectangle. In the cutting step, culture pieces with multiple cut shapes may be produced from one culture, and as specific examples, multiple cut pieces with the same cut shape may be produced from one culture, or multiple cut pieces with different cut shapes may be produced from one culture.

In the cutting step, the first spot diameter formed in a portion to be irradiated in the light-absorbing layer by light is set according to the predetermined shape. The first spot diameter means a diameter of a light beam at a contact portion between the light and the light-absorbing layer. In the case where accurate cutting is required, the first spot diameter is set to be preferably smaller than the spot diameter in the case where accurate cutting is not required, for example. In the case of cutting into a complicated shape, the spot diameter (P1) is set to be preferably smaller than the spot diameter (P2) in the case of cutting into a simple shape such as a circular shape, i.e., P1 and P2 preferably satisfy P1<P2, for example. P1 and P2 can be set, as appropriate, according to the size of the culture, output of the light source, the scanning speed of the spot in a cell treatment, and the like, for example. As a specific example, when an object to be treated is iPS cells, P1 is, for example, 10 μm, and P2 is, for example, 20 μm. In the case where the cutting step is performed using the cell treatment apparatus, the light irradiation position can be moved, for example, by the laser moving device, and the first spot diameter can be adjusted, for example, by the spot diameter adjustment device.

The treating step is a step of irradiating the light-absorbing layer corresponding to a portion other than the region to be cut with light to subject the culture existing above the light-absorbing layer to a killing treatment. The killing treatment may be, for example, a treatment by which the culture is killed and may be performed by destroying the culture. The light irradiation can be described with reference to the description of the light irradiation in the cutting step, for example. The light is preferably laser. When the light is laser, for example, the second spot diameter to be described later can be accurately controlled, and more accurate treatment can be performed.

In the treating step, the second spot diameter formed in a portion to be irradiated in an object to be treated (e.g., a target organism) by light is set according to the treatment. The second spot diameter means a diameter of a light beam at a contact portion between the light and the light-absorbing layer. The second spot diameter is preferably larger than the first spot diameter. With these spot diameters, for example, an object to be treated in a wide range can be treated, and a killing treatment can be performed efficiently in a short time. The ratio (S1:S2) between the first spot diameter (S1) and the second spot diameter (S2) is preferably 1:2 or more. In the treating step, the spot diameter (P3) in the case where a region to be irradiated with light has a simple shape is preferably larger than the spot diameter (P4) in the case where an object to be treated in a region having a complicated shape such as a region with a partition or the like, i.e., P3 and P4 preferably satisfy P3>P4. Thus, comparing the first spot diameters and the second spot diameters in the cutting step and the treating step, the spot diameters preferably satisfy P1<P2<P4<P3. P3 and P4 can be set, as appropriate, according to the size of the culture, output of the light source, the scanning speed of the spot in a cell treatment, and the like, for example. As a specific example, when an object to be treated is iPS cells, P3 is, for example, 100 μm, and P4 is, for example, 40 μm. In the case where the treating step is performed using the cell treatment apparatus, the second spot diameter is adjusted, for example, by the spot diameter adjustment device.

In this manner, the object to be treated can be cut and treated.

Although the present invention is described above with reference to embodiments, the present invention is not limited thereto. Various modifications can be made within the scope of the present invention which can be understood by those skilled in the art.

The present application is based upon and claims the benefit of priority from Japanese patent application No. 2017-24512, filed on Feb. 13, 2017, the entire disclosure of which is incorporated herein its entirety by reference.

INDUSTRIAL APPLICABILITY

The cell treatment apparatus according to the present invention is capable of treating cells in the cell culture vessel.

By the treatment method according to the present invention, an object including a light-absorbing layer and a culture existing above the light-absorbing layer can be treated.

Therefore, the present invention is extremely useful, for example, in the fields of regenerative medicine, drug discovery, and the like in which a large amount of cells with stable quality is used.

REFERENCE SIGNS LIST

100: cell treatment apparatus
1: first region
11*a*, 11*b*: opening
12*a*, 12*b*: door
13*a*: first XY stage
13*b*: arm
14: suction/discharge device
15: light source
16*a*: drainage container placement portion
16*b*: drainage container
16*c*: tip member detachment device
17*a*: storage container placement portion
17*b*: storage container
18: culture vessel placement portion
181: upper lid
182: bottom
183: translucent region
184: cell culture vessel
185: bottom wall
186: bottom plate
187: recess
188: projection
19*a*: collection container placement portion
19*b*: collection container
3: second region
31: second XY stage
311*a*, 311*b*: carriage
32: microscope
321*a*, 321*b*, 321*c*: objective lens
33: laser irradiation device
331: laser light source
332: laser emission unit
333: optical fiber
5: third region
51: control device
51*a*: CPU
51*b*: main memory
51*c*: auxiliary storage device
51*d*: video codec
51*e*: I/O interface
51*f*: controller
52: power supply device
7: circulator
71: intake unit
72: circulation path
73: gas supply unit
74: discharge unit

The invention claimed is:
1. A cell treatment apparatus, comprising:
a first region; and
a second region, wherein
the first region and the second region are placed in succession,
the first region is a cell treatment chamber for treating cells,
the cell treatment chamber is closeable from outside of the cell treatment chamber and comprises a culture vessel placement portion for placing a cell culture vessel,
the second region comprising:
an imaging device that comprises objective lenses;
a laser irradiation device;
and
a spot diameter adjustment device,
wherein
the laser irradiation device comprises a laser light source and a laser emitter, and the laser irradiation device is capable of irradiating the cell culture vessel placed in the culture vessel placement portion with a laser emitted via the laser emitter,
the spot diameter adjustment device adjusts a spot diameter formed in a portion to be irradiated with the laser in an object to be irradiated, the culture vessel placement portion is placed to be adjacent to the second region in the cell treatment chamber, an adjacent portion to the second region in the culture vessel placement portion is translucent, and electric power to the laser irradiation device and the imaging device is supplied from outside of the first region and the second region.

2. The cell treatment apparatus according to claim 1, wherein the laser irradiation device comprises multiple lenses, and the spot diameter adjustment device adjusts the spot diameter by switching among the lenses.

3. The cell treatment apparatus according to claim 1, wherein the spot diameter adjustment device adjusts the spot diameter by adjusting the distance between the laser irradiation device and the object to be irradiated.

4. The cell treatment apparatus according to claim 1, wherein a spot diameter adjustment controller controls the adjustment of the spot diameter performed by the spot diameter adjustment device.

5. The cell treatment apparatus according to claim 1, wherein the first region is placed above the second region.

6. The cell treatment apparatus according to claim 1, wherein the second region comprises the imaging device capable of taking an image of cells in the cell culture vessel placed in the culture vessel placement portion, and the laser irradiation device and the imaging device are configured as independent units.

7. A method for treating an object to be treated, the method comprising:

cutting an object to be treated that includes a light-absorbing layer and a culture existing above the light-absorbing layer by irradiating a region of the light-absorbing layer corresponding to a region to be cut in the culture with light to cut the culture existing above the light-absorbing layer into a predetermined shape; and treating the light-absorbing layer corresponding to a portion other than the region to be cut by irradiating with light to subject the culture existing above the light-absorbing layer to a killing treatment, wherein a first spot diameter formed in a portion to be irradiated with the light in the light-absorbing layer by the light in the cutting step is different from a second spot diameter formed in a portion to be irradiated in the light-absorbing layer by the light in the treating step;

wherein the method is implemented by a cell treatment apparatus that comprises:

a first region; and a second region, wherein the first region and the second region are placed in succession, the first region is a cell treatment chamber for treating cells, the cell treatment chamber is closeable from outside of the cell treatment chamber and comprises a culture vessel placement portion for placing a cell culture vessel, the second region comprises:

a laser irradiation device;

an imaging device; and a spot diameter adjustment device, wherein the laser irradiation device comprises a laser light source and a laser emitter, and the laser irradiation device is capable of irradiating the cell culture vessel placed in the culture vessel placement portion with a laser emitted via the laser emitter, the imaging device comprises objective lenses, the spot diameter adjustment device adjusts a spot diameter formed in a portion to be irradiated with the laser in an object to be irradiated, the culture vessel placement portion is placed to be adjacent to the second region in the cell treatment chamber, an adjacent portion to the second region in the culture vessel placement portion is translucent, and electric power to the laser irradiation device and the imaging device is supplied from outside of the first region and the second region.

8. The method according to claim 7, wherein the first spot diameter is smaller than the second spot diameter.

9. The method according to claim 7, wherein the light is laser.

* * * * *